United States Patent
Asrar et al.

(10) Patent No.: US 6,992,047 B2
(45) Date of Patent: Jan. 31, 2006

(54) METHOD OF MICROENCAPSULATING AN AGRICULTURAL ACTIVE HAVING A HIGH MELTING POINT AND USES FOR SUCH MATERIALS

(75) Inventors: Jawed Asrar, Chesterfield, MO (US); Yiwei Ding, St. Louis, MO (US)

(73) Assignee: Monsanto Technology LLC, St Louis, MO (US)

( * ) Notice: Subject to any disclaimer, the term of this patent is extended or adjusted under 35 U.S.C. 154(b) by 354 days.

(21) Appl. No.: 10/115,765

(22) Filed: Apr. 3, 2002

(65) Prior Publication Data

US 2003/0022791 A1 Jan. 30, 2003

Related U.S. Application Data

(60) Provisional application No. 60/283,053, filed on Apr. 11, 2001.

(51) Int. Cl.
*A01N 25/28* (2006.01)
*A01N 43/10* (2006.01)
*A01N 55/10* (2006.01)

(52) U.S. Cl. .................. 504/359; 424/497; 514/63; 514/383; 514/448; 514/963

(58) Field of Classification Search ............... 504/359; 424/497; 514/63, 383, 448, 963
See application file for complete search history.

(56) References Cited

U.S. PATENT DOCUMENTS

| | | | |
|---|---|---|---|
| 3,516,846 A | 6/1970 | Matson | 117/36.2 |
| 3,516,941 A | 6/1970 | Matson | 252/316 |
| 4,285,720 A | 8/1981 | Scher | 71/88 |
| 4,599,271 A | 7/1986 | Chao | 428/402.21 |
| 4,640,709 A | 2/1987 | Beestman | 71/100 |
| 4,643,764 A | 2/1987 | Scher | 71/100 |
| 4,681,806 A | 7/1987 | Matkan et al. | 428/402.21 |
| 4,738,898 A | 4/1988 | Vivant | 428/402.21 |
| 4,889,719 A | 12/1989 | Ohtsubo et al. | 424/408 |
| 4,938,797 A * | 7/1990 | Hasslin et al. | 504/359 |
| 4,956,129 A | 9/1990 | Scher et al. | 264/4.7 |
| 5,006,161 A | 4/1991 | Hasslin et al. | 71/118 |
| 5,306,712 A | 4/1994 | Tobitsuka et al. | 514/63 |
| 5,310,721 A | 5/1994 | Lo | 504/116 |
| 5,482,974 A | 1/1996 | Phillion et al. | 514/619 |
| 5,486,621 A | 1/1996 | Phillion et al. | 549/4 |
| 5,498,630 A | 3/1996 | Phillion et al. | 514/443 |
| 5,693,667 A | 12/1997 | Phillion et al. | 514/461 |
| 5,705,513 A | 1/1998 | Phillion et al. | 514/354 |
| 5,811,411 A | 9/1998 | Phillion et al. | 514/63 |
| 5,834,447 A | 11/1998 | Phillion et al. | 514/63 |
| 5,849,723 A | 12/1998 | Phillion et al. | 514/63 |
| 5,925,464 A * | 7/1999 | Mulqueen et al. | 428/402.2 |
| 5,925,595 A * | 7/1999 | Seitz et al. | 504/359 |
| 5,994,270 A | 11/1999 | Phillion et al. | 504/193 |
| 5,998,466 A | 12/1999 | Phillion et al. | 514/443 |
| RE36,562 E | 2/2000 | Phillion et al. | 514/443 |
| 6,028,101 A | 2/2000 | Phillion et al. | 514/469 |
| 6,037,478 A | 3/2000 | Fevig et al. | 549/4 |
| 6,084,108 A | 7/2000 | Fevig et al. | 549/61 |
| 6,133,197 A | 10/2000 | Chen et al. | 504/116 |
| 6,133,252 A | 10/2000 | Phillion et al. | 514/189 |
| 2003/0114308 A1 * | 6/2003 | De Billot et al. | 504/116.1 |

FOREIGN PATENT DOCUMENTS

| | | |
|---|---|---|
| EP | 0008207 A2 | 2/1980 |
| EP | 0252896 A2 | 1/1988 |
| EP | 0369614 A1 | 5/1990 |
| EP | 0538231 A1 | 4/1993 |
| WO | WO 9524380 | 9/1995 |
| WO | WO 00/27200 | 5/2000 |

OTHER PUBLICATIONS

International Search Report for International Application No. PCT/US 02/10551, dated Sep. 18, 2002.

* cited by examiner

*Primary Examiner*—S. Mark Clardy
(74) *Attorney, Agent, or Firm*—Nelson Mullins Riley & Scarborough LLP

(57) ABSTRACT

A method of producing a controlled release form of an agricultural active material includes the provision of an organic liquid composition in which the active is present, but where the liquid composition is free from aromatic solvents and is maintained below the normal melting point of the active. The liquid composition is formed into small droplets and the droplets are enclosed by a non-water soluble shell to provide microcapsules, the shell of which is designed to release the agricultural active at a pre-selected controlled rate when the microcapsule is exposed to natural environmental conditions. Controlled release forms of agricultural actives are also provided.

51 Claims, 8 Drawing Sheets

METHOD OF MICROENCAPSULATING AN AGRICULTURAL ACTIVE HAVING A HIGH MELTING POINT AND USES FOR SUCH MATERIALS

BACKGROUND OF THE INVENTION (1) Field of the Invention

The present invention relates to methods for the microencapsulation of an agricultural active having a high melting point, and more particularly to methods for the microencapsulation of such material while maintaining the temperature of the agricultural active below its normal melting point and without contacting the active with an aromatic solvent.

(2) Description of the Related Art

Materials that affect the growth and development of agronomically important plants, or that provide some type of protection of plants from pests and diseases, are commonly referred to as agricultural actives. Such materials are widely used in modern agriculture and provide benefits of increased yield, vigor and overall plant health. However, some agricultural actives have harmful effects if they are ingested or otherwise contacted by humans or other animals.

The most common method for using agricultural actives is direct application of the active to a plant, seed, or to the soil in which the plant is to be grown. But wind, runoff and groundwater leaching can cause undesirable movement of the active, which can result in its unintended contact with plants and animals in streams, neighboring fields and homes. Furthermore, such movement of the active from the zone where protection is desired can result in reduction of the concentration of the active to below efficacious levels by the time the target pest arrives. Irreversible binding of the active to components of soil exacerbates this problem.

One method to improve the delivery and safety characteristics of agricultural actives is to include them as components of a controlled release composition. Many different types of such controlled release compositions are known and include the encapsulation of droplets, the formation of a coating on solid particles, and the inclusion of actives in matrix microparticles. Such formulations typically place coatings of a barrier material between the active and the environment through which the active must move in order to reach the environment. The rate at which such transfer takes place depends upon the type of coating, its thickness, the chemical affinity of the active for the matrix, as well as many environmental parameters, such as temperature, moisture levels, and the like.

Thus, encapsulation of an active can improve its safety and stability, its dispersibility and even distribution, its handling characteristics, as well as to control its release rate.

Although both solid particles and liquids can be enclosed in coatings, the formation of microcapsules around liquid droplets is believed to have several advantages over the coating of solid particles. For example, microcapsules formed around liquid droplets have regular spherical geometry, coatings of even thickness, and lack sharp edges and concave surfaces, which can occur in coatings of solid particles, and which could cause uneven coating thickness or even lack of a coating on some parts of the active. A coating having a regular geometry and an even thickness provides more predictable release characteristics than an uneven coating of varying thickness.

A number of methods for the encapsulation of liquid droplets containing agricultural actives is known in the art, and a summary of such methods is provided, for example, in *Controlled-Release Delivery Systems for Pesticides*, H. B. Scher, Ed., Marcel Dekker, Inc., New York (1999); in *Microencapsulation*, S. Benita, Ed., Marcel Dekker, New York (1996); and in *Microencapsulation and Related Drug Processes*, Patrick B. Deasy, Ed., Marcel Dekker, New York (1984).

Matson, in U.S. Pat. Nos. 3,516,846 and 3,516,941 and Sher et al., in U.S. Pat. No. 4,956,129, describe the formation of a urea-formaldehyde polymer coating around small liquid droplets.

Another commonly used method for the encapsulation of liquid droplets involves the generation of a polyurea shell around an active-containing core by interfacial polymerization at the surface of the droplets. Advantages of using a polyurea shell include that the material is generally nonphytotoxic, its permeability characteristics can be controlled, and the shell can be formed at relatively low temperatures—in fact, polymerization temperatures of lower than 90° C. are almost always used, and temperatures of from about 40° C.–70° C., are preferred.

In U.S. Pat. Nos. 4,285,720 and 4,643,764, Scher describes a process involving the blending of various pesticides with an organic polyisocyanate to form an organic phase, which is dispersed into small droplets into an aqueous phase. Some molecules of the organic polyisocyanate hydrolyze to form amines, which then can react with other isocyanates to form the polyurea shell.

Chao, in U.S. Pat. No. 4,599,271, describes the use of two or more organic-in-aqueous emulsions for the formation of a polyurea shell around a polyisocyanate containing droplet.

Beestman (in U.S. Pat. No. 4,640,709) discloses the inclusion of an alkylated polyvinyl pyrrolidone polymer that acts as an emulsifier in the aqueous phase of a two-phase system which is capable of providing microcapsules having high levels of an enclosed water-immiscible material.

In U.S. Pat. No. 4,681,806, Matkan et al. describe particles containing a releasable fill material and having a polyurea surface layer that encloses a polyurea matrix having the fill material contained therein.

Ohtsubo et al. (in U.S. Pat. No. 4,889,719) describe the microencapsulation of organophosphorous insecticidal compositions by the formation of a polyurea shell. Similar methods have been used for the microencapsulation of herbicidally active N-chloroacetylcyclohexeneamines and herbicidally active chloroacetanilide in a polyurea shell, and are described in U.S. Pat. No. 5,006,161, to Hasslin et al.

In U.S. Pat. No. 4,738,898, Vivant describes microencapsulation of a variety of materials within polyurea skin membranes by interfacial polyaddition involving a polyisocyanato hydrophobic liquid in an essentially aqueous medium. The polyisocyanato hydrophobic liquid contained the dissolved material to be encapsulated, an aliphatic diisocyanate and an isocyanurate ring trimer of an aliphatic diisocyanate. The isocyanate materials were reacted with a polyamine to form a polyurea shell material. The microcapsules described by Vivant had leakproof walls that were designed for the microencapsulation of colorants and the production of pressure-sensitive carbonless paper, for example. The microcapsules were designed to maintain the encapsulated material until the capsule was ruptured, and would not have been suitable for the controlled release of the encapsulated materials through the walls of the capsule.

Hasslin et al. (in U.S. Pat. No. 4,938,797) describes the encapsulation of a water-immiscible pesticide in a polyurea shell. The method includes the use of an anionic dispersant, such as a salt of polystyrenesulfonic acid in the aqueous phase. A similar method is described in U.S. Pat. No. 5,310,721, to Lo, but all of the agricultural active materials that are encapsulated are liquids at ambient temperature.

Seitz et al. (in U.S. Pat. No. 5,925,595) disclose a process for the preparation of microencapsulated materials—including low-melting herbicides, such as acetanilides—by combining a triisocyanate and a diisocyanate with a water immiscible composition which can include the herbicide; forming a dispersion of the core chemical and the blend of isocyanates in an aqueous liquid; and reacting the isocyanates with a polyamine to form microcapsules.

In U.S. Pat. No. 6,133,197, Chen et al., describe the formation of quick release microcapsules containing an agriculturally active material and having a polyurea shell with relatively low degree of cross-linking.

Despite the advantages provided by microcapsules having polyurea shells that enclose liquid cores containing agricultural actives, the methods that are known for the formation of these structures have certain limitations that limit their use with certain highly promising actives. For example, if the agricultural active has a melting point that is close to, or higher than, the preferred range of polymerization temperature for polyurea shell formation, it is difficult to liquify the active in order to form the microcapsule. A common solution to this situation has been to dissolve the active in an aromatic solvent. See, e.g., WO 00/27200, where the formation of a slow release capsule suspension is described wherein a mixture of a fungicide (thienol[2,3-d]pyrimidin-4-one) and another agricultural active (selected from a list of possible materials) is blended with polyisocyanates in an aromatic solvent. This organic phase is emulsified in an aqueous liquid phase, and 1,6-diaminohexane is added to cause a polymerization reaction with the isocyanates to form microcapsules that enclose the mixture of agricultural actives.

Since many aromatic solvents are phytotoxic, their use in controlled release formulations intended for application to plants or seeds would appear to be potentially harmful to the plant.

One new class of agricultural actives that appears to be very promising for fungicidal and other applications is described in U.S. Pat. Nos. 5,482,974, 5,486,621, 5,498,630, 5,693,667, 5,693,667, 5,705,513, 5,811,411, 5,834,447, 5,849,723, 5,994,270, 5,998,466, 6,028,101, and in publications WO 93/07751, and EP 0 538 231 A1. One such compound, in particular, is 4,5-dimethyl-N-(2-propenyl)-2-(trimethylsilyl)-3-thiophenecarboxamide, having a CAS registration number of 175217-20-6, and for which the proposed ISO common name is "Silthiopham". Silthiopham has a normal melting point of about 86° C.–88° C., which has limited its incorporation into polyurea microcapsules by known techniques. Further information about silthiopham can be found in U.S. Pat. No. 5,486,621.

Accordingly, it would be useful to provide a method for the formation of microcapsules enclosing such high-melting agricultural actives where the method was free of the use of aromatic solvents—and preferably free of any solvents—and where the method could be carried out at a temperature that was below the normal melting point of the active. It would also be useful if such method allowed for the use of a polyurea shell that could be designed to release the active from the microcapsule at a controlled rate when the microcapsule was exposed to natural environmental conditions.

SUMMARY OF THE INVENTION

Briefly, therefore the present invention is directed to a novel method of producing a controlled release form of a first agricultural active having a normal melting point, the method comprising providing an organic liquid composition comprising a first agricultural active having low water solubility where the composition is free of aromatic solvents; forming the liquid composition into small droplets while maintaining said liquid composition at a temperature below the normal melting point of the first agricultural active; and enclosing each droplet in a non-water soluble shell to form a microcapsule. When desired, the shell can be designed to release the first agricultural active from the microcapsule at a pre-selected controlled rate when the microcapsule is exposed to natural environmental conditions.

The present invention is also directed to a novel controlled release form of an agricultural active comprising a compound having the formula

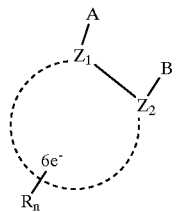

wherein $Z_1$ and $Z_2$ are C or N and are part of an aromatic ring selected from benzene, pyridine, thiophene, furan, pyrrole, pyrazole, thiazole, and isothiazole;

A is selected from —C(X)-amine, —C(O)—$SR_3$, —NH—C(X)$R_4$, and —C(=$NR_3$)—$XR_7$;

B is —$W_m$-Q($R_2$)$_3$ or selected from o-tolyl, 1-naphthyl, 2-naphthyl, and 9-phenanthryl, each optionally substituted with halogen or $R_4$;

Q is C, Si, Ge, or Sn;

W is —C($R_3$)$_p$H$_{(2-p)}$—; or when Q is C, W is selected from —C($R_3$)$_p$H$_{(2-p)}$—, —N($R_3$)$_m$H$_{(1-m)}$—, —S(O)$_p$—, and —O—;

X is O or S;

n is 0, 1, 2, or 3;

m is 0 or 1;

p is 0, 1, or 2;

each R is independently selected from a) halo, formyl, cyano, amino, nitro, thiocyanato, isothiocyanato, trimethylsilyl, and hydroxy;

b) C1–C4 alkyl, alkenyl, alkynyl, C3–C6 cycloalkyl, and cycloalkenyl, each optionally substituted with halo, hydroxy, thio, amino, nitro, cyano, formyl, phenyl, C1–C4 alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;

c) phenyl, furyl, thienyl, pyrrolyl, each optionally substituted with halo, formyl, cyano, amino, nitro, C1–C4 alkyl, alkenyl, alkynyl, alkoxy, alkylthio, alkylamino, dialkylamino, haloalkyl, and haloalkenyl;

d) C1–C4 alkoxy, alkenoxy, alkynoxy, C3–C6 cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo;

wherein two R groups may be combined to form a fused ring;

each $R_2$ is independently selected from alkyl, alkenyl, alkynyl, cycloalkyl, cycloalkenyl and phenyl, each optionally substituted with $R_4$ or halogen; and wherein, when Q is C, $R_2$ may also be selected from halo, alkoxy, alkylthio, alkylamino, and dialkylamino;
wherein two $R_2$ groups may be combined to form a cyclo group with Q;
$R_3$ is C1–C4 alkyl;
$R_4$ is C1–C4 alkyl, haloalkyl, alkoxy, alkylthio, alkylamino, or dialkylamino;
$R_7$ is C1–C4 alkyl, haloalkyl, or phenyl, optionally substituted with halo, nitro, or $R_4$;
or an agronomic salt thereof.

The present invention is also drawn to a novel method of reducing the melting point of an agricultural active material having the formula

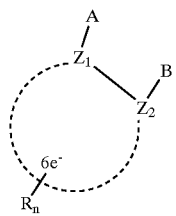

wherein $Z_1$ and $Z_2$ are C or N and are part of an aromatic ring selected from benzene, pyridine, thiophene, furan, pyrrole, pyrazole, thiazole, and isothiazole;
A is selected from —C(X)-amine, —C(O)—$SR_3$, —NH—C(X)$R_4$, and —C(=$NR_3$)—$XR_7$;
B is —$W_m$-Q($R_2$)$_3$ or selected from o-tolyl, 1-naphthyl, 2-naphthyl, and 9-phenanthryl, each optionally substituted with halogen or $R_4$;
Q is C, Si, Ge, or Sn;
W is —C($R_3$)$_p$H$_{(2-p)}$—; or when Q is C, W is selected from —C($R_3$)$_p$H$_{(2-p)}$—, —N($R_3$)$_m$H$_{(1-m)}$—, —S(O)$_p$—, and —O—;
X is O or S;
n is, 1, 2, or 3;
m is 0 or 1;
p is 0, 1, or 2;
each R is independently selected from
  a) halo, formyl, cyano, amino, nitro, thiocyanato, isothiocyanato, trimethylsilyl, and hydroxy;
  b) C1–C4 alkyl, alkenyl, alkynyl, C3–C6 cycloalkyl, and cycloalkenyl, each optionally substituted with halo, hydroxy, thio, amino, nitro, cyano, formyl, phenyl, C1–C4 alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;
  c) phenyl, furyl, thienyl, pyrrolyl, each optionally substituted with halo, formyl, cyano, amino, nitro, C1–C4 alkyl, alkenyl, alkynyl, alkoxy, alkylthio, alkylamino, dialkylamino, haloalkyl, and haloalkenyl;
  d) C1–C4 alkoxy, alkenoxy, alkynoxy, C3–C6 cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo;
wherein two R groups may be combined to form a fused ring;
each $R_2$ is independently selected from alkyl, alkenyl, alkynyl, cycloalkyl, cycloalkenyl and phenyl, each optionally substituted with $R_4$ or halogen; and wherein, when Q is C, $R_2$ may also be selected from halo, alkoxy, alkylthio, alkylamino, and dialkylamino;
wherein two $R_2$ groups may be combined to form a cyclo group with Q;
$R_3$ is C1–C4 alkyl;
$R_4$ is C1–C4 alkyl, haloalkyl, alkoxy, alkylthio, alkylamino, or dialkylamino;
$R_7$ is C1–C4 alkyl, haloalkyl, or phenyl, optionally substituted with halo, nitro, or $R_4$;
or an agronomic salt thereof, comprising mixing said agricultural active material with tebuconazole or simeconazole.

The present invention is also directed to a novel controlled release form of an agricultural active comprising a compound having the formula

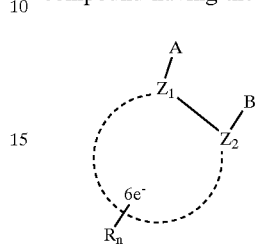

wherein $Z_1$ and $Z_2$ are C or N and are part of an aromatic ring selected from benzene, pyridine, thiophene, furan, pyrrole, pyrazole, thiazole, and isothiazole;
A is selected from —C(X)-amine, —C(O)—$SR_3$, —NH—C(X)$R_4$, and —C(=$NR_3$)—$XR_7$;
B is —$W_m$-Q($R_2$)$_3$ or selected from o-tolyl, 1-naphthyl, 2-naphthyl, and 9-phenanthryl, each optionally substituted with halogen or $R_4$;
Q is C, Si, Ge, or Sn;
W is —C($R_3$)$_p$H$_{(2-p)}$—; or when Q is C, W is selected from —C($R_3$)$_p$H$_{(2-p)}$—, —N($R_3$)$_m$H$_{(1-m)}$—, —S(O)$_p$—, and —O—;
X is O or S;
n is 0, 1, 2, or 3;
m is 0 or 1;
p is 0, 1, or 2;
each R is independently selected from
  a) halo, formyl, cyano, amino, nitro, thiocyanato, isothiocyanato, trimethylsilyl, and hydroxy;
  b) C1–C4 alkyl, alkenyl, alkynyl, C3–C6 cycloalkyl, and cycloalkenyl, each optionally substituted with halo, hydroxy, thio, amino, nitro, cyano, formyl, phenyl, C1–C4 alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;
  c) phenyl, furyl, thienyl, pyrrolyl, each optionally substituted with halo, formyl, cyano, amino, nitro, C1–C4 alkyl, alkenyl, alkynyl, alkoxy, alkylthio, alkylamino, dialkylamino, haloalkyl, and haloalkenyl;
  d) C1–C4 alkoxy, alkenoxy, alkynoxy, C3–C6 cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo;
wherein two R groups may be combined to form a fused ring;
each $R_2$ is independently selected from alkyl, alkenyl, alkynyl, cycloalkyl, cycloalkenyl and phenyl, each optionally substituted with $R_4$ or halogen; and wherein, when Q is C, $R_2$ may also be selected from halo, alkoxy, alkylthio, alkylamino, and dialkylamino;
wherein two $R_2$ groups may be combined to form a cyclo group with Q;
$R_3$ is C1–C4 alkyl;
$R_4$ is C1–C4 alkyl, haloalkyl, alkoxy, alkylthio, alkylamino, or dialkylamino;

R$_7$ is C1–C4 alkyl, haloalkyl, or phenyl, optionally substituted with halo, nitro, or R$_4$;
or an agronomic salt thereof, and
a structure which controls the release of said compound.

The present invention is also directed to a novel microcapsule comprising a polyurea shell enclosing a core which comprises silthiopham, where the microcapsule has an average size of from about 2µ to about 8µ where the weight ratio of the shell to the core is from about 15:100 to about 30:100, and where the amount of silthiopham in the core is from about 30% to about 60%, by weight.

The present invention is also directed to a novel method of producing a microencapsulated form of a high melting material which method is free of the use of solvents, the method comprising mixing a high melting material and a melting point depressant to form a composition which is free of solvents; heating the composition to a temperature at which the composition is a liquid, but which temperature is below the normal melting points of both the high melting material and the melting point depressant; forming the liquid composition into small droplets while maintaining said liquid composition at a temperature below the normal melting points of both the high melting material and the melting point depressant; and enclosing each droplet in a non-water soluble shell by interfacial polymerization to form a microcapsule.

Among the several advantages found to be achieved by the present invention, therefore, may be noted the provision of a method for the formation of microcapsules enclosing high-melting agricultural actives where the method was free of the use of aromatic solvents and where the method could be carried out at a temperature that was below the normal melting point of the active, and the provision of a method that allowed for the use of a polyurea shell that could be designed to release the active from the microcapsule at a controlled rate when the microcapsule was exposed to natural environmental conditions.

DETAILED DESCRIPTION OF THE PREFERRED EMBODIMENTS

Figure 1:
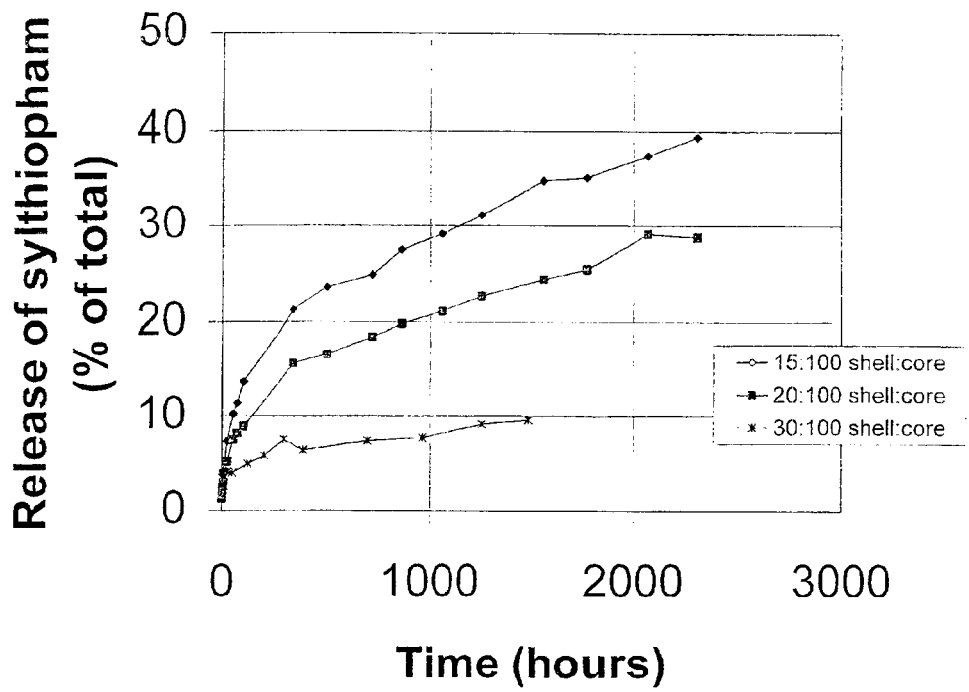
FIG. 1 is a release rate profile showing the release of silthiopham as a function of time and as a function of shell wall thickness for microcapsules of the present invention having 40% silthiopham in the core, where profiles are shown for microcapsules having shell:core weight ratios of 15:100, 20:100, and 30:100.

In accordance with the present invention, it has been discovered that microcapsules containing a high-melting agricultural active material (as those terms are defined below) can be produced without raising the temperature of the active to its normal melting point and without the use of an aromatic solvent. The microcapsules can have an outer shell that is formed of polyurea and the microcapsules can be designed to release the active from the microcapsule at a pre-selected controlled rate when the microcapsule is exposed to natural environmental conditions.

In one embodiment, this disclosure describes the microencapsulation of a first agricultural active, such as silthiopham, in a polyurea shell, where the encapsulation is achieved by an interfacial polymerization process. Two processes are disclosed for preparing the emulsion necessary for the interfacial polymerization, one involves encapsulation of the active in solution in a non-aromatic organic solvent and the other involves encapsulation of a blend of the active and a melting point depressant.

The embodiment of the present invention involving the production of microcapsules that contain silthiopham in the core and which are free of non-aromatic solvents, is believed to be particularly advantageous. It is believed that such microcapsules, applied to wheat seed in the fall, could provide an initial level of protection sufficient to protect the seed from harmful biological activity until temperatures fall low enough that biological pressure becomes insignificant for the winter, but would retain a sufficient amount of the active so that it would still be releasing at a sufficient level in the spring to provide protection against the increasing biological pressure throughout sprouting and initial growth of the plant. This type of protection from only one seed treatment with the novel microcapsules would provide protection for the seeds and the plants and would save at least one, and perhaps two, conventional field applications of a pesticide.

As will be discussed in detail below, it has been found that the novel microcapsules can be designed to provide a pre-selected controlled rate of release of an enclosed active, by controlling, among other parameters, the active loading in the core, the thickness of the shell wall, the particle size, and the composition of the shell wall. This ability to control the release profile permits the tailoring of the microcapsules to meet a wide range of application demands. As would be understood by one having skill in the art, the release rate of the encapsulated active material would be affected by such environmental parameters as temperature and moisture. However, one can use the controllable parameters described above to provide a desired release rate for any particular set of environmental conditions. For example, if one knew the geographic location in which the novel material was to be used, it would be possible to predict the temperature to be expected during the different seasons, and to design a material that would provide a certain release rate at the predicted temperatures.

One embodiment of the present invention advantageously extends the state of the art to include the encapsulation of almost any high melting solid by a method that includes interfacial polymerization, but without the necessity of using a solvent to dissolve the high melting solid. In U.S. Pat. No. 5,310,721, to Lo, it is taught that microcapsules prepared by interfacial polycondensation can advantageously contain materials which have a variety of uses, such as for dyes, inks, color formers, pharmaceuticals, cosmetics, flavoring materials, agricultural chemicals, and the like. The Lo patent states that any liquid, oil, low melting solid, or solvent-soluble material into which a first wall-forming material can be dissolved and which is non-reactive with said wall-forming material may be encapsulated with this technique.

The present invention extends the state of the art to include the encapsulation of almost any high melting solid by forming a mixture of the high melting solid with a melting point depressant that is a solid at conventional interfacial polymerization temperatures (for polyurea formation, this is about 50° C.–90° C.), but is capable of combining with the high melting solid to form a eutectic mixture, where the melting point of the eutectic mixture is sufficiently low to permit the mixture to be encapsulated by known interfacial polymerization techniques, such as referred to in the Lo patent. It is preferable, but not required, that the melting point depressant is a material of the same type as the high melting solid. For example, it is particularly advantageous when both are dyes, inks, pharmaceuticals, flavoring materials, agricultural chemicals, and the like.

As used herein, a "material having a high normal melting point", which is also referred to herein as a "high melting material", is a material which has a normal melting point temperature that is higher than the upper limit of the temperature range that is conventionally used to carry out the interfacial polymerization method that is being used to form the encapsulating shell around the material. For example, when the interfacial polymerization method comprises the formation of a polyurea shell, the preferred temperature range that is conventionally used is about 50° C. to about 90° C., more preferably, about 50° C. to about 80° C., even more preferably, about 50° C. to about 70° C., and yet more preferably, about 50° C. to about 60° C. Therefore, a high melting material, in this instance, is one having a normal melting point that is above 90° C., or above the upper limit of another of the preferred ranges.

It is preferred that the first agricultural active, the high melting material, and the melting point depressant, are materials that have a low water solubility. When it is said that such a material has a "low water solubility", or is "non-water soluble", it is meant that such material has a solubility in water at 25° C. of less than about 1%, by weight. It is preferred that the water solubility is less than about 0.1%, by weight, more preferred that it is less than about 0.01% by weight, yet more preferred that it is less than about 0.001% by weight, and even more preferred that it is less than about 0.0001% by weight.

When the material having a high normal melting point is an agricultural active, the terms "high-melting point agricultural active", or "high-melting active", as used herein, mean an agricultural active having a normal melting point that is the same as described above for a high melting material. In general, a high-melting agricultural active materials is one that is difficult to encapsulate neat by conventional methods for forming a polyurea shell around a core of the active.

The "normal melting point" of a material, as those terms are used herein, refers to the temperature at which the solid form of the material is in equilibrium with the liquid form at atmospheric pressure. It is understood that such terms include the description of materials—such as some polymers—which sometimes have a range of temperature over which melting occurs. In these cases, the normal melting point of a polymer can be understood to be any temperature within the normal melting range for the polymer; commonly it is a temperature at or near the mid-point of the melting range. For example, a material having a normal melting range of 86° C.–88° C., could be said to have a normal melting point of about 87° C.

Agricultural active materials that are suitable for use in the present invention include the compounds described in U.S. Pat. Nos. 5,482,974, 5,486,621, 5,498,630, 5,693,667, 5,693,667, 5,705,513, 5,811,411, 5,834,447, 5,849,723, 5,994,270, 5,998,466, 6,028,101, and in publications WO 93/07751, and EP 0 538 231 A1. In particular, such compounds are described in U.S. Pat. No. 5,693,667 and in European Patent Application No. 0 538 231 A1, which describe compounds having the formula

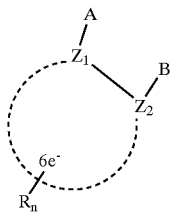

wherein $Z_1$ and $Z_2$ are C or N and are part of an aromatic ring selected from benzene, pyridine, thiophene, furan, pyrrole, pyrazole, thiazole, and isothiazole;
A is selected from —C(X)-amine, —C(O)—SR$_3$, —NH—C(X)R$_4$, and —C(=NR$_3$)—XR$_7$;
B is —W$_m$-Q(R$_2$)$_3$ or selected from o-tolyl, 1-naphthyl, 2-naphthyl, and 9-phenanthryl, each optionally substituted with halogen or R$_4$;
Q is C, Si, Ge, or Sn;
W is —C(R$_3$)$_p$H$_{(2-p)}$—; or when Q is C, W is selected from —C(R$_3$)$_p$H$_{(2-p)}$—, —N(R$_3$)$_m$H$_{(1-m)}$—, —S(O)$_p$—, and —O—;
X is O or S;
n is 0, 1, 2, or 3;
m is 0 or 1;
p is 0, 1, or 2;
each R is independently selected from
  a) halo, formyl, cyano, amino, nitro, thiocyanato, isothiocyanato, trimethylsilyl, and hydroxy;
  b) $C_1$–$C_4$ alkyl, alkenyl, alkynyl, $C_3$–$C_6$ cycloalkyl, and cycloalkenyl, each optionally substituted with halo, hydroxy, thio, amino, nitro, cyano, formyl, phenyl, $C_1$–$C_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;
  c) phenyl, furyl, thienyl, pyrrolyl, each optionally substituted with halo, formyl, cyano, amino, nitro, $C_1$–$C_4$ alkyl, alkenyl, alkynyl, alkoxy, alkylthio, alkylamino, dialkylamino, haloalkyl, and haloalkenyl;
  d) $C_1$–$C_4$ alkoxy, alkenoxy, alkynoxy, $C_3$–$C_6$ cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo;
wherein two R groups may be combined to form a fused ring;
each $R_2$ is independently selected from alkyl, alkenyl, alkynyl, cycloalkyl, cycloalkenyl and phenyl, each optionally substituted with $R_4$ or halogen; and wherein, when Q is C, $R_2$ may also be selected from halo, alkoxy, alkylthio, alkylamino, and dialkylamino;
wherein two $R_2$ groups may be combined to form a cyclo group with Q;
$R_3$ is $C_1$–$C_4$ alkyl;
$R_4$ is $C_1$–$C_4$ alkyl, haloalkyl, alkoxy, alkylthio, alkylamino, or dialkylamino;
$R_7$ is $C_1$–$C_4$ alkyl, haloalkyl, or phenyl, optionally substituted with halo, nitro, or $R_4$;
or an agronomic salt thereof.

The term "amine" in —C(X)-amine means an unsubstituted, monosubstituted, or disubstituted amino radical, including nitrogen-bearing heterocycles. Examples of substituents for the amino radical include, but are not limited to, hydroxy; alkyl, alkenyl, and alkynyl, which may be straight or branched chain or cyclic; alkoxyalkyl; haloalkyl; hydroxyalkyl; alkylthio; alkylthioalkyl; alkylcarbonyl; alkoxycarbonyl; aminocarbonyl; alkylaminocarbonyl; cyanoalkyl; mono- or dialkylamino; phenyl, phenylalkyl or phenylalkenyl, each optionally substituted with one or more $C_1$–$C_6$ alkyl, alkoxy, haloalkyl, $C_3$–$C_6$ cycloalkyl, halo, or nitro groups; $C_1$–$C_4$ alkyl or alkenyl groups substituted with heterocycles, optionally substituted with one or more $C_1$–$C_4$ alkyl, alkoxy, haloalkyl, halo, or nitro groups. Examples of such nitrogen-bearing heterocycles, which are bonded at a nitrogen to —C(X)—, include, but are not limited to, morpholine, piperazine, piperidine, pyrrole, pyrrolidine, imidazole, and triazoles, each of which may be optionally substituted with one or more $C_1$–$C_6$ alkyl groups.

Specific examples of the amino radicals useful in the present invention include, but are not limited to, ethylamino, methylamino, propylamino, 2-methylethylamino, 1-propenylamino, 2-propenylamino, 2-methyl-2-propenylamino, 2-propynylamino, butylamino, 1,1-dimethyl-2-propynylamino, diethylamino, dimethylamino, N-(methyl)ethylamino, N-(methyl)-1,1(dimethyl)ethylamino, dipropylamino, octylamino, N-(ethyl)-1-methylethylamino, 2-hydroxyethylamino, 1-methylpropylamino, chloromethylamino, 2-chloroethylamino, 2-bromoethylamino, 3-chloropropylamino, 2,2,2-trifluoroethylamino, cyanomethyl, methylthiomethylamino, (methylsulfonyl)oxyethylamino, 2-ethoxyethylamino, 2-methoxyethylamino, N-(ethyl)-2-ethoxyethylamino, 1-methoxy-2,2-dimethylpropylamino, cyclopropylamino, cyclobutylamino, cyclopentylamino, cyclohexylamino, methoxymethylamino, N-(methoxymethyl)ethylamino, N-(1-methylethyl)propylamino, 1-methylheptylamino, N-(ethyl)-1-methylheptylamino, 6,6-dimethyl-2-hepten-4-ynylamino, 1,1-dimethyl-2-propynylamino. Further examples include benzylamino, ethylbenzylamino, 3-methoxybenzylamino, 3-(trifluoromethyl)benzylamino, N-methyl-3-(trifluoromethyl)benzylamino, 3,4,5-trimethoxybenzylamino, 1,3-benzodioxol-5-ylmethylamino, phenylamino, 3-(1-methylethyl)phenylamino, ethoxyphenylamino, cyclopentylphenylamino, methoxyphenylamino, nitrophenylamino, 1-phenylethylamino, N-(methyl)-3-phenyl-2-propenylamino, benzotriazolylphenylmethyl, 2-pyridinylmethylamino, N-(ethyl)-2-pyridinylmethylamino, 2-thienylmethylamino, and furylmethylamino. Further examples of amino radicals include methylhydrazino, dimethylhydrazino, N-ethylanilino, and 2-methylanilino. The amine may also be substituted with diethyl N-ethylphosphoramidic acid, t-butoxycarbonyl, methoxycarbonyl, ethoxycarbonyl, propoxycarbonyl, etc. Of these examples of the amino radical, ethylamino is preferred.

Examples of B include, but are not limited to, trimethylsilyl, ethyldimethylsilyl, diethylmethylsilyl, triethylsilyl, dimethylpropylsilyl, dipropylmethylsilyl, dimethyl-1-(methyl)ethylsilyl, tripropylsilyl, butyldimethylsilyl, pentyidimethylsilyl, hexyldimethylsilyl, cyclopropyldimethylsilyl, cyclobutyldimethylsilyl, cyclopentyidimethylsilyl, cyclohexyldimethylsilyl, dimethylethenylsilyl, dimethylpropenylsilyl, chloromethyldimethylsilyl, 2-chloroethyldimethylsilyl, bromomethyldimethylsilyl, bicycloheptyldimethylsilyl, dimethylphenylsilyl, dimethyl-2-(methyl)phenylsilyl, dimethyl-2-fluorophenylsilyl, and other such silyl groups of the formula Si(R$_2$)$_3$; any such silyl group connected to the Z$_1$–Z$_2$ ring by a methylene group; and any of these groups wherein germanium or tin is substituted for silicon. Of these examples of B, trimethylsilyl is preferred.

Further examples of B include 1,1-dimethylethyl, 1,1-dimethylpropyl, 1,1-dimethylbutyl, 1,1-dimethylpentyl, 1-ethyl-1-methylbutyl, 2,2-dimethylpropyl, 2,2-dimethylbutyl, 1-methyl-1-ethylpropyl, 1,1-diethylpropyl, 1,1,2-trimethylpropyl, 1,1,2-trimethylbutyl, 1,1,2,2-tetramethylpropyl, 1,1-dimethyl-2-propenyl, 1,1,2-trimethyl-2-propenyl, 1,1-dimethyl-2-butenyl, 1,1-dimethyl-2-propynyl, 1,1-dimethyl-2-butynyl, 1-cyclopropyl-1-methylethyl, 1-cyclobutyl-1-methylethyl, 1-cyclopentyl-1-methylethyl, 1-(1-cyclopentenyl)-1-methylethyl, 1-cyclohexyl-1-methylethyl, 1-(1-cyclohexenyl)-1-methylethyl, 1-methyl-1-phenylethyl, 1,1-dimethyl-2-chloroethyl, 1,1-dimethyl-3-chloropropyl, 1,1-dimethyl-2-methoxyethyl, 1,1-dimethyl-2-(methylamino)ethyl, 1,1-dimethyl-2-(dimethylamino)ethyl, 1,1-dimethyl-3-chloro-2-propenyl, 1-methyl-1-methoxyethyl, 1-methyl-1-(methylthio)ethyl, 1-methyl-1-(methylamino)ethyl, 1-methyl-1-(dimethylamino)ethyl, 1-chloro-1-methylethyl, 1-bromo-1-methylethyl, and 1-iodo-1-methylethyl. Of these examples of B, 1,1-dimethylethyl is preferred.

Further examples of B are 1,1-dimethylethylamino, 1,1-dimethylpropylamino, 1,1-dimethylbutylamino, 1,1-dimethylpentylamino, 1-ethyl-1-methylbutylamino, 2,2-dimethylpropylamino, 2,2-dimethylbutylamino, 1-methyl-1-ethylpropylamino, 1,1-diethylpropylamino, 1,1,2-trimethylpropylamino, 1,1,2-trimethylbutylamino, 1,1,2,2-tetramethylpropylamino, 1,1-dimethyl-2-propenylamino, 1,1,2-trimethyl-2-propenylamino, 1,1-dimethyl-2-butenylamino, 1,1-dimethyl-2-propynylamino, 1,1-dimethyl-2-butynylamino, 1-cyclopropyl-1-methylethylamino, 1-cyclobutyl-1-methylethylamino, 1-cyclopentyl-1-methylethylamino, 1-(1-cyclopentenyl)-1-methylethylamino, 1-cyclohexyl-1-methylethylamino, 1-(1-cyclohexenyl)-1-methylethylamino, 1-methyl-1-phenylethylamino, 1,1-dimethyl-2-chloroethylamino, 1,1-dimethyl-3-chloropropylamino, 1,1-dimethyl-2-methoxyethylamino, 1,1-dimethyl-2-(methylamino)ethylamino, 1,1-dimethyl-2-(dimethylamino)ethylamino, and 1,1-dimethyl-3-chloro-2-propenylamino. Any of these groups may also have a methyl substitution on the nitrogen, as in N-(methyl)-1,1-dimethylethylamino and N-(methyl)-1,1-dimethylpropylamino. Of these examples of B, 1,1-dimethylethylamino and N-(methyl)-1,1-dimethylethylamino are preferred.

Further examples of B include 1,1-dimethylethoxy, 1,1-dimethylpropoxy, 1,1-dimethylbutoxy, 1,1-dimethylpentoxy, 1-ethyl-1-methylbutoxy, 2,2-dimethylpropoxy, 2,2-dimethylbutoxy, 1-methyl-1-ethylpropoxy, 1,1-diethylpropoxy, 1,1,2-trimethylpropoxy, 1,1,2-trimethylbutoxy, 1,1,2,2-tetramethylpropoxy, 1,1-dimethyl-2-propenoxy, 1,1,2-trimethyl-2-propenoxy, 1,1-dimethyl-2-butenoxy, 1,1-dimethyl-2-propynyloxy, 1,1-dimethyl-2-butynyloxy, 1-cyclopropyl-1-methylethoxy, 1-cyclobutyl-1-methylethoxy, 1-cyclopentyl-1-methylethoxy, 1-(1-cyclopentenyl)-1-methylethoxy, 1-cyclohexyl-1-methylethoxy, 1-(1-cyclohexenyl)-1-methylethoxy, 1-methyl-1-phenylethoxy, 1,1-dimethyl-2-chloroethoxy, 1,1-dimethyl-3-chloropropoxy, 1,1-dimethyl-2-methoxyethoxy, 1,1-dimethyl-2-(methylamino)ethoxy, 1,1-dimethyl-2-(dimethylamino)ethoxy, 1,1-dimethyl-3-chloro-2-propenoxy. Of these examples of B, 1,1-dimethylethoxy is preferred.

Further examples of B include 1 methylcyclopropyl, 1-methylcyclobutyl, 1-methylcyclopentyl, 1-methylcyclohexyl, 1-methylcyclopropylamino, 1-methylcyclobutylamino, 1-methylcyclopentylamino, 1-methylcyclohexylamino, N-(methyl)-1-methylcyclopropylamino, N-(methyl)-1-methylcyclobutylamino, N-(methyl)-1-methylcyclopentylamino, and N-(methyl)-1-methylcyclohexylamino.

R$_n$ may be any substituent(s) which do(es) not unduly reduce the effectiveness of the compounds to function in the method of disease control. R$_n$ is generally a small group; "n" is preferably 1 for benzene rings and 2 for furan and thiophene. R is more preferably methyl or halogen, and more preferably is located adjacent to A.

When Z$_1$ and Z$_2$ are part of a benzene ring, the following are not included as useful active agents of the present invention: 1) n is not zero when B is trimethylsilyl and A is N,N-diethylaminocarbonyl, N,N-bis(1-methylethyl)aminocarbonyl, N-methylaminothiocarbonyl, N-ethylaminocarbonyl, 1-piperidinylcarbonyl, or N-phenylaminocarbonyl; or when B is orthotolyl and A is N,N-diethylaminocarbonyl, N,N-bis(1methylethyl)aminocarbonyl, N-methylaminocarbonyl, or O-methylcarbamyl; or when B is 1,1-dimethylethyl and A is N,N-dimethylaminothiocarbonyl or N-phenylaminocarbonyl; or when B is trimethylstannyl and A is N,N-diethylaminocarbonyl or O-(1,1-dimethylethyl) carbamyl; 2) when B is 2-trimethylsilyl and A is N,N-diethylaminocarbonyl, R$_n$ is not 3-fluoro-6-formyl, 3-fluoro-6methyl, 3-chloro-6-formyl, 3-fluoro, 3-chloro, 3-chloro-6-methyl, 6-trimethylsilyl, or 6-methyl; 3) when A is O-(1,1-dimethylethyl)carbamyl and B is 2-trimethylsilyl, R$_n$ is not 5-trifluoromethyl; 4) when A is N-phenylaminocarbonyl and B is 2,2-dimethylpropyl, R$_n$ is not 3-methyl; and 5) R is not isothiocyanato when A is —C(O)-amine and W$_m$ is —O—.

When Z$_1$ and Z$_2$ are part of a thiophene, furan or pyrrole ring, the novel compounds of the present invention do not include B equal to trimethylsilyl when A is (diethylamino) carbonyl.

Useful agricultural actives of the type described above have also been described in U.S. Pat. No. 5,998,466 as a compound having the formula

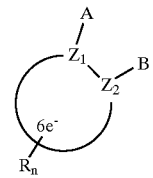

wherein Z$_1$ and Z$_2$ are C or N and are part of an aromatic ring which is thiophene;

A is selected from —C(X)-amine, wherein the amine is substituted with a first and a second amine substituent or with an alkylaminocarbonyl and a hydrogen, —C(O)—SR$_3$, —NH—C(X)R$_4$, and —C(=NR$_3$)—XR$_7$;

the first amine substituent which is selected from the group consisting of C$_1$–C$_{10}$ straight or branched alkyl, alkenyl, or alkylaryl groups or mixtures thereof optionally substituted with one or more halogen, hydroxy, alkoxy, alkylthio, nitrile, alkylsulfonate, haloalkylsulfonate, phenyl, C$_3$–C$_6$ cyclocalkyl and C$_5$–C$_6$ cycloalkynel; phenyl optionally substituted with one or more C$_1$–C$_4$ straight or branched alkyl, alkenyl, or alkynyl groups or mixtures thereof, cycloalkyl, cycloalkenyl, haloalkyl, alkoxy and nitro; C$_3$–C$_6$ cycloalkyl, C$_5$–C$_6$ cycloalkenyl, alkoxy, alkenoxy, alkynoxy, dialkylamino, and alkylthio;

and the second amine substituent which is selected from the group consisting of hydrogen; $C_1$–$C_6$ straight or branched alkyl, alkenyl, or alkynyl groups or mixtures thereof optionally substituted with one or more halogen; hydroxy, alkylcarbonyl, haloalkylcarbonyl, alkoxycarbonyl, and dialkylcarbonyl;

B is —$W_m$-Q($R_2$)$_3$ or selected from o-tolyl, 1-naphthyl, 2-naphthyl, and 9-phenanthryl, each optionally substituted with halogen or $R_4$;

Q is C, Si, Ge, or Sn;

W is —C($R_3$)$_p$H$_{(2-p)}$—; or when Q is C, W is selected from —C($R_3$)$_p$H$_{(2-p)}$—, —N($R_3$)$_m$H$_{(1-m)}$—, —S(O)$_p$—, and —O—;

X is O or S;

n is 2;

m is 0 or 1;

p is 0, 1, or 2;

wherein two R groups are combined to form a nonheterocyclic ring fused with the thiophene ring, which is not a benzothiophene other than a tetrahydrobenzothiophene, said two R groups being selected from the group consisting of $C_1$–$C_4$ alkyl, alkenyl, $C_3$–$C_6$ cycloalkyl and cycloalkenyl, each optionally substituted with hydroxy, thio, phenyl, $C_1$–$C_4$ alkoxy, alkylthio, alkylsulfinyl, or alkylsulfonyl;

each $R_2$ is independently selected from alkyl, alkenyl, alkynyl, cycloalkyl, cycloalkenyl and phenyl, each optionally substituted with $R_4$ or halogen; and wherein, when Q is C, $R_2$ may also be selected from halo, alkoxy, alkylthio, alkylamino, and dialkylamino; and further when Q is C, then two $R_2$ groups may be combined to form a cycloalkyl group with Q;

$R_3$ is $C_1$–$C_4$ alkyl;

$R_4$ is $C_1$–$C_4$ alkyl, haloalkyl, alkoxy, alkylthio, alkylamino, or dialkylamino; and $R_7$ is $C_1$–$C_4$ alkyl, haloalkyl, or phenyl optionally substituted with halo, nitro, or $R_4$;

or an agronomic salt thereof.

The terms "amine", "alkyl", "alkoxy", "alkoxyalkyl", "monoalkylamino", "dialkylamino", "haloalkyl", and "halo", and B, $R_n$, and the features of $Z_1$ and $Z_2$, are as described above.

Agricultural actives that are useful in the present invention can also be selected from those described in U.S. Pat. No. 5,482,974, namely, a compound having the formula

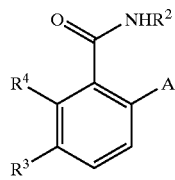

wherein $R_2$ is ethyl, iso-propyl, propyl or allyl;

A is N(CH$_3$)$_{1-n}$H$_n$R$^5$ or OR$^6$ wherein n is 0 or 1, R$^5$ is (CH$_3$)$_m$(CH$_3$CH$_2$)$_{3-m}$C, 1-methyl-1-cyclopentyl, 1-methyl-1-cyclohexyl or 2, 3-dimethyl-2-butyl wherein m is 0, 1, 2 or 3 and R$^6$ is independently R$^5$, or 2,3,3-trimethyl-2-butyl;

R$^3$ is H or independently R$^4$; and

R$^4$ is halo or CH$_3$;

with the proviso that when A is N(CH$_3$)$_{1-n}$H$_n$R$^5$, if R$^3$ is H and R$^5$ is 1-methyl-1-cyclohexyl or (CH$_3$)$_m$(CH$_2$CH$_3$)$_{3-m}$C, where m is 0 or 3, or if R$^3$ is halo and R$^2$ is (CH$_3$)$_m$(CH$_3$CH$_2$)$_{3-m}$C, where m is 3, then R$^2$ cannot be ethyl;

and with the proviso that when A is OR$^6$ then m is equal to or less than 2, and if R$^3$ is H or halo and R$^2$ is ethyl or isopropyl, then R$^6$ is (CH$_3$)$_M$(CH$_3$CH$_2$)$_{3-M}$C where m is 1;or an agronomic salt thereof.

Active agents that are useful in the present invention can also be selected from those described in U.S. Pat. No. 5,994,270, namely, a compound having the formula (a)
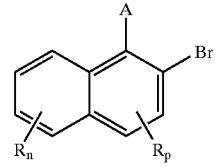

(b)
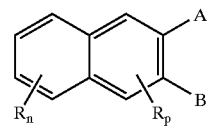

(c)
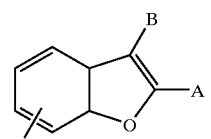

(d)
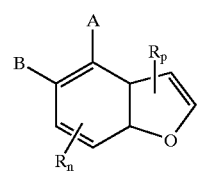

(e)
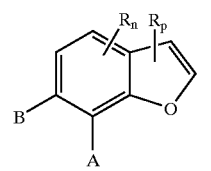

(f)
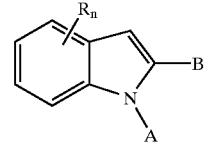

(g)
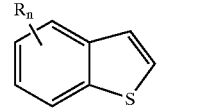

(h)
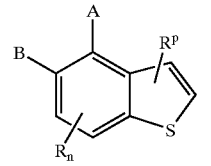

(i)
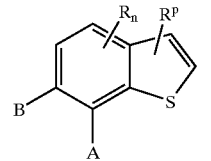

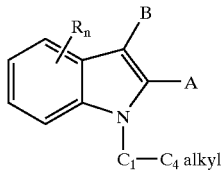

(j)

where A is —C(X)-amine; B is —W$_m$-Q(R$_2$)$_3$; and A can be B when B is A except when the formula is f), then Q cannot be Si;

Q is C or Si;
W is —NH—, —O— or NCH$_3$;
X is O or S;
m is 0 or 1, provided that m is 0 when Q is Si;
n is 0, 1, 2, or 3
p is 0, 1 or 2, and n plus p is equal to or less than 3; each R is independently selected from a) halo, formyl, cyano, amino, nitro, thiocyanato, isothiocyanato, trimethylsilyl, and hydroxy;

b) C$_1$–C$_4$ alkyl, alkenyl, alkynyl, C$_3$–C$_6$ cycloalkyl, and cycloalkenyl, each optionally substituted with halo, hydroxy, thio, amino, nitro, cyano, formyl, phenyl, C$_1$–C$_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;

c) phenyl, furyl, thienyl, pyrrolyl, each optionally substituted with halo, formyl, cyano, amino, nitro, C$_1$–C$_4$ alkyl, alkenyl, alkynyl, alkoxy, alkylthio, alkylamino, dialkylamino, haloalkyl, and haloalkenyl;

d) C$_1$–C$_4$ alkoxy, alkenoxy, alkynoxy, C$_3$–C$_6$ cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo; each R$_2$ is independently selected from alkyl, alkenyl, alkynyl, cycloalkyl, cycloalkenyl and phenyl, each optionally substituted with R$_4$ or halogen; and wherein, when Q is C, R$_2$ may also be selected from halo, alkoxy, alkylthio, alkylamino, and dialkylamino; wherein two R$_2$ groups may be combined to form a cyclo group with Q; R$_4$ is C$_1$–C$_4$ alkyl, haloalkyl, alkoxy, alkylthio, alkylamino, or dialkylamino; or an agronomic salt thereof.

The term "amine" in —C(X)-amine means an unsubstituted, monosubstituted, or disubstituted amino radical, including nitrogen-bearing heterocycles. Examples of substituents for the amino radical include, but are not limited to, hydroxy; alkyl, alkenyl, and alkynyl, which may be straight or branched chain or cyclic; alkoxyalkyl; haloalkyl; hydroxyalkyl; alkylthio; alkylthioalkyl; alkylcarbonyl; alkoxycarbonyl; aminocarbonyl; alkylaminocarbonyl; cyanoalkyl; mono- or dialkylamino; phenyl, phenylalkyl or phenylalkenyl, each optionally substituted with one or more C$_1$–C$_6$ alkyl, alkoxy, haloalkyl, C$_3$–C$_6$ cycloalkyl, halo, or nitro groups; C$_1$–C$_4$ alkyl or alkenyl groups substituted with heterocycles, optionally substituted with one or more C$_1$–C$_4$ alkyl, alkoxy, haloalkyl, halo, or nitro groups. Examples of such nitrogen-bearing heterocycles, which are bonded at a nitrogen to —C(X)—, include, but are not limited to, morpholine, piperazine, piperidine, pyrrole, pyrrolidine, imidazole, and triazoles, each of which may be optionally substituted with one or more C$_1$–C$_6$ alkyl groups.

Specific examples of the amino radicals useful in the present invention include, but are not limited to, ethylamino, methylamino, propylamino, 2-methylethylamino, 1-propenylamino, 2-propenylamino, 2-methyl-2-propenylamino, 2-propynylamino, butylamino, 1,1-dimethyl-2-propynylamino, diethylamino, dimethylamino, N-(methyl)ethylamino, N-(methyl)-1,1-(dimethyl)ethylamino, dipropylamino, octylamino, N-(ethyl)-1-methylethylamino, 2-hydroxyethylamino, 1-methylpropylamino, chloromethylamino, 2-chloroethylamino, 2-bromoethylamino, 3-chloropropylamino, 2,2,2-trifluoroethylamino, cyanomethyl, methylthiomethylamino, (methylsulfonyl)oxyethylamino, 2-ethoxyethylamino, 2-methoxyethylamino, N-(ethyl)-2-ethoxyethylamino, 1-methoxy-2,2-dimethylpropylamino, cyclopropylamino, cyclobutylamino, cyclopentylamino, cyclohexylamino, methoxymethylamino, N-(methoxymethyl)ethylamino, N-(1-methylethyl)propylamino, 1-methylheptylamino, N-(ethyl)-1-methylheptylamino, 6,6-dimethyl-2-hepten-4-ynylamino, 1,1-dimethyl-2-propynylamino. Further examples include benzylamino, ethylbenzylamino, 3-methoxybenzylamino, 3-(trifluoromethyl)benzylamino, N-methyl-3-(trifluoromethyl)benzylamino, 3,4,5-trimethoxybenzylamino, 1,3-benzodioxol-5-ylmethylamino, phenylamino, 3-(1-methylethyl)phenylamino, ethoxyphenylamino, cyclopentylphenylamino, methoxyphenylamino, nitrophenylamino, 1-phenylethylamino, N-(methyl)-3-phenyl-2-propenylamino, benzotriazolylphenylmethyl, 2-pyridinylmethylamino, N-(ethyl)-2-pyridinylmethylamino, 2-thienylmethylamino, and furylmethylamino.

Further examples of amino radicals include methylhydrazino, dimethylhydrazino, N-ethylanilino, and 2-methylanilino. The amine may also be substituted with diethyl N-ethylphosphoramidic acid, t-butoxycarbonyl, methoxycarbonyl, ethoxycarbonyl, propoxycarbonyl, etc. Of these examples of the amino radical, ethylamino, propylamino, or allylamino is preferred.

Examples of B include, but are not limited to, trimethylsilyl, ethyldimethylsilyl, diethylmethylsilyl, triethylsilyl, dimethylpropylsilyl, dipropylmethylsilyl, dimethyl-1-(methyl)ethylsilyl, tripropylsilyl, butyldimethylsilyl, pentyidimethylsilyl, hexyldimethylsilyl, cyclopropyldimethylsilyl, cyclobutyldimethylsilyl, cyclopentyidimethylsilyl, cyclohexyldimethylsilyl, dimethylethenylsilyl, dimethylpropenylsilyl, chloromethyldimethylsilyl, 2-chloroethyldimethylsilyl, bromomethyldimethylsilyl, bicycloheptyldimethylsilyl, dimethylphenylsilyl, dimethyl-2-(methyl)phenylsilyl, dimethyl-2-fluorophenylsilyl, and other such silyl groups of the formula Si(R$_2$)$_3$. Of these examples of B, trimethylsilyl is preferred.

Further examples of B include 1,1-dimethylethyl, 1,1-dimethylpropyl, 1,1-dimethylbutyl, 1,1-dimethylpentyl, 1-ethyl-1-methyl butyl, 2,2-dimethyl propyl, 2,2-dimethylbutyl, 1-methyl-1-ethylpropyl, 1,1-diethylpropyl, 1,1,2-trimethylpropyl, 1,1,2-trimethylbutyl, 1,1,2,2-tetramethylpropyl, 1,1-dimethyl-2-propenyl, 1,1,2-trimethyl-2-propenyl, 1,1-dimethyl-2-butenyl, 1,1-dimethyl-2-propynyl, 1,1-dimethyl-2-butynyl, 1-cyclopropyl-1-methylethyl, 1-cyclobutyl-1-methylethyl, 1-cyclopentyl-1-methylethyl, 1-(1-cyclopentenyl)-1-methylethyl, 1-cyclohexyl-1-methylethyl, 1-(1-cyclohexenyl)-1-methylethyl, 1-methyl-1-phenylethyl, 1,1-dimethyl-2-chloroethyl, 1,1-dimethyl-3-chloropropyl, 1,1-dimethyl-2-methoxyethyl, 1,1-dimethyl-2-(methylamino)ethyl, 1,1-dimethyl-2-(dimethylamino)ethyl, 1,1-dimethyl- 3-chloro-2-propenyl, 1-methyl-1-methoxyethyl, 1-methyl-1-(methylthio)ethyl, 1-methyl-1-(methylamino)ethyl, 1-methyl-1-(dimethylamino)ethyl, 1-chloro-1-methylethyl, 1-bromo-1-methylethyl, and 1-iodo-1-methylethyl. Of these examples of B, 1,1-dimethylpropyl, 1,1-diethylethyl or 1-methyl-1-cyclopentyl is preferred.

Further examples of B are 1,1-dimethylethylamino, 1,1-dimethylpropylamino, 1,1-dimethylbutylamino, 1,1-dimethylpentylamino, 1-ethyl-1-methylbutylamino, 2,2-dimethylpropylamino, 2,2-dimethylbutylamino, 1-methyl-1-ethylpropylamino, 1,1-diethylpropylamino, 1,1,2-trimethylpropylamino, 1,1,2-trimethylbutylamino, 1,1,2,2-tetramethylpropylamino, 1,1-dimethyl-2-propenylamino, 1,1,2-trimethyl-2-propenylamino, 1,1-dimethyl-2-butenylamino, 1,1-dimethyl-2-propynylamino, 1,1-dimethyl-2-butynylamino, 1-cyclopropyl-1-methylethylamino, 1-cyclobutyl-1-methylethylamino, 1-cyclopentyl-1-methylethylamino, 1-(1-cyclopentenyl)-1-methylethylamino, 1-cyclohexyl-1-methylethylamino, 1-(1-cyclohexenyl)-1-methylethylamino, 1-methyl-1-phenylethylamino, 1,1-dimethyl-2-chloroethylamino, 1,1-dimethyl-3-chloropropylamino, 1,1-dimethyl-2-methoxyethylamino, 1,1-dimethyl-2-(methylamino)-ethylamino, 1,1-dimethyl-2-(dimethylamino)ethylamino, and 1,1-dimethyl-3-chloro-2-propenylamino. Of these examples of B, 1,1-dimethylpropylamino, 1,1-ethylethylamino or 1-methyl-1-cyclopentylamino is preferred.

Further examples of B include 1,1-dimethylethoxy, 1,1-dimethylpropoxy, 1,1-dimethylbutoxy, 1,1-dimethylpentoxy, 1-ethyl-1-methylbutoxy, 2,2-dimethylpropoxy, 2,2-dimethylbutoxy, 1-methyl-1-ethylpropoxy, 1,1-diethylpropoxy, 1,1,2-trimethylpropoxy, 1,1,2-trimethylbutoxy, 1,1,2,2-tetramethylpropoxy, 1,1-dimethyl-2-propenoxy, 1,1,2-trimethyl-2-propenoxy, 1,1-dimethyl-2-butenoxy, 1,1-dimethyl-2-propynyloxy, 1,1-dimethyl-2-butynyloxy, 1-cyclopropyl-1-methylethoxy, 1-cyclobutyl-1-methylethoxy, 1-cyclopentyl-1-methylethoxy, 1-(1-cyclopentenyl)-1-methylethoxy, 1-cyclohexyl-1-methylethoxy, 1-(1-cyclohexenyl)-1-methylethoxy, 1-methyl-1-phenylethoxy, 1,1-dimethyl-2-chloroethoxy, 1,1-dimethyl-3-chloropropoxy, 1,1-dimethyl-2-methoxyethoxy, 1,1-dimethyl-2-(methylamino)ethoxy, 1,1-dimethyl-2-(dimethylamino)ethoxy, 1,1-dimethyl-3-chloro-2-propenoxy. Of these examples of B, 1,1-dimethylpropyloxy, 1,1-diethylethyloxy or cyclopentyloxy is preferred.

Further examples of B include 1-methylcyclopropyl, 1-methylcyclobutyl, 1-methylcyclopentyl, 1-methylcyclohexyl, 1-methylcyclopropylamino, 1-methylcyclobutylamino, 1-methylcyclopentylamino, and 1-methylcyclohexylamino.

$R_n$ may be any substituent(s) which do(es) not unduly reduce the effectiveness of the compounds to function in the method of control of *Gaeumannomyces graminis* var. *tritici*. $R_n$ is generally a small group; "n" is preferably 0 or 1. R is preferably methyl or halogen.

As used to describe the compounds discussed just above, the term "alkyl", unless otherwise indicated, means an alkyl radical, straight or branched chain, having, unless otherwise indicated, from 1 to 10 carbon atoms. The terms "alkenyl" and "alkynyl" mean unsaturated radicals having from 2 to 7 carbon atoms. Examples of such alkenyl groups include ethenyl, 1-propenyl, 2-propenyl, 1-butenyl, 2-butenyl, 3-butenyl, 2-methyl-1-propenyl, 2-methyl-2-propenyl, 1-methylethenyl, and the like. Examples of such alkynyl groups include ethynyl, 1-propynyl, 2-propynyl, 1,1-dimethyl-2-propynyl, and so forth. Substituent groups may also be both alkenyl and alkynyl, for example, 6,6-dimethyl-2-hepten-4-ynyl.

As used to describe the compounds discussed just above, the term "alkoxy" means an alkyl group having, unless otherwise indicated, from 1 to 10 carbon atoms connected via an ether linkage. Examples of such alkoxy groups include methoxy, ethoxy, propoxy, 1-methylethoxy, and so forth.

As used to describe the compounds discussed just above, the term "alkoxyalkyl" means an ether radical having, unless otherwise indicated, from 1 to 10 carbon atoms. Examples of such alkoxyalkyl groups include methoxymethyl, methoxyethyl, ethoxymethyl, ethoxyethyl, and so forth.

As used to describe the compounds discussed just above, the terms "monoalkylamino" and "dialkylamino" each mean an amino group having, respectively, 1 or 2 hydrogens replaced with an alkyl group.

As used to describe the compounds discussed just above, the term "haloalkyl" means an alkyl radical having one or more hydrogen atoms replaced by halogens, including radicals having all hydrogen atoms substituted by halogen. Examples of such haloalkyl groups are fluoromethyl, difluoromethyl, trifluoromethyl, chloromethyl, trichloromethyl, and so forth.

As used to describe the compounds discussed just above, the term "halo" means a radical selected from chloro, bromo, fluoro, and iodo.

A preferred active agent is a compound having the structure 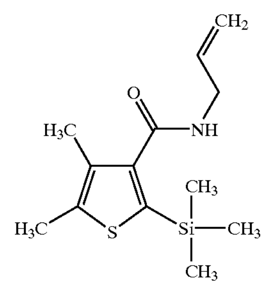 and which is known as 4,5-dimethyl-N-(2-propenyl)-2-(trimethylsilyl)-3-thiophenecarboxamide, having a CAS registration number of 175217-20-6, and for which the proposed ISO common name is "Silthiopham", or "Sylthiopham". In this specification, this active agent may be referred to as silthiopham.

In this specification, the agricultural actives that are described above can be referred to as a "first agricultural active". In another embodiment, the first agricultural active can include simeconazole.

The first agricultural active material of the present invention can be used in any purity that passes for such material in the commercial trade. The material can be used in any form in which it is received from the supplier, or in which it is synthesized. However, if a solvent is present, such solvents are non-aromatic organic liquid solvents that are among those that are described herein below.

When the first agricultural active is mixed with a solvent in order to form an organic phase that is a liquid at temperatures lower than the normal melting point of the first agricultural active, the solvent can be a non-aromatic organic liquid in which the active is soluble in a amount of at least about 5%, by weight, at 70° C. Preferably, the solvent is one in which the active is soluble in an amount of at least about 20%, by weight, more preferably at least about 40%, by weight, even more preferably at least about 50%, by weight, and yet more preferably at least about 60%, by weight, all at a temperature of 70° C.

It is preferred that the solvent has a normal boiling point that is higher than the upper level of the normal range of temperature that is commonly used for the polymerization reaction of the encapsulation method that is being used. A boiling point of at least about 20° C. above this upper level is preferred, at least about 30° C. above this upper level is even more preferred, and at least about 50° C. above this upper level is yet more preferred.

Suitable solvents for the present method can be found in *Organic Solvents Physical Properties and Method of Purification*, by Riddick, J. A., W. B. Bunger and T. K. Sakano, John Wiley & Sons, New York (1984) and can be selected from hydrocarbons, hydroxy compounds (but excluding alcohols that react more rapidly with the isocyanates that are used in the synthesis of the shell material than such isocyanates react with the amines that are used), ethers, carbonyls, acids, esters, halogenated hydrocarbons, polychlorinated hydrocarbons, brominated hydrocarbons, iodinated hydrocarbons, mixed halogenated hydrocarbons, nitro compounds, amides, sulfides, thioethers, oxo-sulfur compounds, and compounds having more than one type of characteristic atom or group. It is preferred that the solvent for use in the present method be selected from hydrocarbons, hydroxycompounds, ethers, carbonyls, esters and compounds with more than one type of characteristic atom or group.

When the solvent is a hydrocarbon, saturated aliphatic hydrocarbons such as, for example, decane, octane and dodecane, and unsaturated hydrocarbons (excluding those having an aromatic group) and including, for example, i-dodecane, 2-pinene, camphene, limonene, and the like, are useful.

Examples of hydroxy compounds that are useful include aliphatic alcohols that are not water soluble, such as cyclohexanol, 1-octanol, and the like.

Examples of ethers that are useful include aliphatic ethers that are not water soluble, such as dibutyl ether and the like.

Examples of carbonyls include camphor and the like.

Examples of esters include butyl acetate, glyceryl triacetate, butyl stearate, hexyl acetate, acetyltri-n-butyl citrate and diethyl adipate, and the like. A preferred solvent is acetyltri-n-butyl citrate (which is available under the trade name Citroflex A-4, from Morflex, Inc., Greensboro, N.C.).

When the liquid composition that contains the first agricultural active is formed by mixing the active with a solvent, it is preferred that the mixture contains at least about 5% by weight of the active, more preferred is about 25%, and even more preferred is about 50% by weight of the active. It is usually desirable to accommodate as much of the active ingredient in the core material as possible in order to extend the useful life of the microcapsules in normal use, however, as will be discussed below, it is sometimes necessary to provide the active at a level that is lower than the maximum amount possible in order to obtain the release rate characteristics that are desired.

When the active material is silthiopham, it is generally preferred to have from about 5% to about 90% by weight of silthiopham in the core, from about 10% to about 80% by weight is more preferred, from 20% to about 70% is yet more preferred, and from about 30% to about 60% by weight is even more preferred in order to obtain a desirable combination of release rate and duration of release.

When the first agricultural active is mixed with a solvent in order to form the liquid composition that will form the core of the microparticles, other agricultural actives—in addition to the first active—can also be added to the mixture. The second, or subsequent, agricultural active can be almost any agricultural active, but is preferably a pesticide or herbicide. The second active is more preferably an insecticide, acaracide, bactericide, fungicide, nematocide or molluscicide. When the second active is a fungicide, it is preferably selected from a group consisting of tebuconazole, tetraconazole, simeconazole, difenoconazole, fluquinconazole, fludioxonil, captan, metalaxyl, carboxin, and thiram.

When the second, or subsquent, agricultural active is a herbicide, it can be selected from the following useful herbicides:

growth regulators, including
  phenoxy acetic acids, such as, 2,4-D and MCPA,
  phenoxy propionic acids, such as, dichlorprop and mecoprop,
  phenoxy butyric acids, such as, 2,4-DB and MCPB,
  benzoic acids, such as, dicamba,
  picolinic acid and related compounds, such as, picloram, triclopyr, clopyralid and quinclorac;
inhibitors of auxin transport, including
  naptalam,
  semicarbones, such as, diflufenzopyr-sodium,
  s-triazines, such as, atrazine, simazine, cyanazine, prometon, ametryn and prometryn,
  other triazines, such as, hexazinone and metribuzin,
  substituted ureas, such as, diuron, fluometuron, linuron and tebuthiuron,
  uracils, such as, bromacil and terbacil,
  benzothiadiazoles, such as, bentazon,
  benzonitroles, such as, bromoxymil,
  phenylcarbamates, such as, desmediphram and phenmedipham,
  pyridazinones, such as, pyrazon,
  phenypyriddazines, such as, pyridate, and
  others, such as, propanil;
pigment inhibitors, including
  amitrole, clomazone and fluridone,
  pyridazinones, such as, norflurazon,
  isoxazoles, such as, isoxaflutole;
growth inhibitors, including
mitotic disruptors, of the types,
  dinitroanilines, such as, benefin, ethalfluralin, oryzalin, pendimethalin, prodiamine and trifluralin,
  oxysulfurons, such as, fluthiamide,
  pyridines, such as, dithiopyr and thiazopyr,
  amides, such as, pronamide, and
  others, such as, DCPA;
  inhibitors of shoots of emerging seedlings, of the types,
    carbamothioates, such as, EPTC, cycloate, pebulate, triallate, butylate, molinate, thiobencarb and bernolate;
  inhibitors of roots only of seedlings, of the types,
    amides, such as, napropamide,
    phenylureas, such as, siduron, and
    others, such as bensulide, betasan and bensumec;
inhibitors of roots and shoots of seedlings, of the types,
  chloroacetamides, such as, acetochlor, dimetenamid, propachlor, alachlor and metolachlor;
inhibitors of amino acid synthesis, including,
  inhibitors of aromatic amino acid synthesis, such as, glyphosate and sulfosate,
  inhibitors of branched chain amino acid synthesis, of the types,
    sulfonylureas, such as, bensulfuron, chlorsulfuron, halosulfuron, nicosulfuron, prosulfuron, fimsulfuron, thifensulfuron, tribenuron, chlorimuron, ethametsulfuron, metsulfuron, primisulfuron, oxasulfuron, sulfometuron, triasulfuron and triflusulfuron, imidazolinones, such as, imazamethabenz, imazamox, imazapic, imazapyr, imazaquin and imazethapyr, triazolopyrimidines, such as, chloransulam and flumetsulam, tyrimidinyloxybenzoates, such as, pyrithiobac;

lipid biosynthesis inhibitors, including, aryoxyphenoxyproprionates, such as, ciclofop-methyl, fenoxaprop-ethyl, fenoxaprop-p-ethyl, fluazifop-p-butyl, haloxyfop and quizalofop-p-ethyl, cyclohexanediones, such as, clethodim, sethoxydim and tralkoxydim;

inhibitors of cell wall biosynthesis, including, nitriles, such as, dichlobenil, benzamides, such as, isoxaben, and others, such as, quinclorac;

cell membrane disrupters, including, dilute sulfuric acid, monocarbamide dihydrogen sulfate and herbicidal oils, bipyridyliums, such as, diquat and paraquat, diphenylethers, such as, acifluorfen, fomesafen, lactofen and oxyfluorfen, oxidiazoles, such as, fluthiacet and oxadiazon, N-phenylheterocycles, such as carfentrazone, flumiclorac and sulfentrazone;

inhibitors of glutamine synthetase, such as glufosinate; and others, such as, DSMA, MSMA, asulam, endothall, ethofumesate, difenzoquat and TCA.

An alternative method for providing the liquid composition containing the agricultural active comprises intermixing the first agricultural active with a melting point depressant in order to form an organic phase that is a liquid at temperatures below the normal melting point of the active. A melting point depressant of the present invention is a material that, when intermixed with the first agricultural active, is capable of forming a eutectic mixture having a melting point that is lower than the melting point of both the first agricultural active and the melting point depressant. It is preferred that the melting point depressant is one that has a normal melting point that is above normal ambient temperature. As used herein, a "eutectic mixture" is a mixture of two or more materials having the lowest melting point that is obtainable by varying the proportions of the components.

The inventors have found that, surprisingly, certain agricultural active materials, other than the first agricultural actives described above, can act as the melting point depressant of the present method. In this specification any agricultural active, other than the first agricultural actives that are described above, can be referred to as a second agricultural active. When a second agricultural active acts as a melting point depressant, such active can be a pesticide or herbicide, and can be selected from insecticides, acaricides, bactericides, fungicides, nematocides, molluscicides, and the like.

When a fungicide is used as the melting point depressant, such fungicides as tebuconazole, simeconazole, fludioxonil, fluquinconazole, difenoconazole, 4,5-dimethyl-N-(2-propenyl)-2-(trimethylsilyl)-3-thiophenecarboxamide (sylthiopham), hexaconazole, etaconazole, propiconazole, triticonazole, flutriafol, epoxiconazole, fenbuconazole, bromuconazole, penconazole, imazalil, tetraconazole, flusilazole, metconazole, diniconazole, myclobutanil, triadimenol, bitertanol, pyremethanil, cyprodinil, tridemorph, fenpropimorph, kresoxim-methyl, azoxystrobin, ZEN90160, fenpiclonil, benalaxyl, furalaxyl, metalaxyl, R-metalaxyl, orfurace, oxadixyl, carboxin, prochloraz, trifulmizole, pyrifenox, acibenzolar-S-methyl, chlorothalonil, cymoaxnil, dimethomorph, famoxadone, quinoxyfen, fenpropidine, spiroxamine, triazoxide, BAS50001F, hymexazole, pencycuron, fenamidone, guazatine, and cyproconazole, are suitable for use. Fungicides such as tebuconazole, simeconazole, difenoconazole, tetraconazole, fluquinconazole, fludioxonil, captan, metalaxyl, carboxin and thiram, are preferred.

When a herbicide is used as the melting point depressant, the herbicide can be selected from the list of herbicides that are described above as being appropriate for use as a second or subsequent agricultural active.

In one preferred embodiment of the present method the liquid composition includes silthiopham as a first agricultural active and the silthiopham is intermixed with a second agricultural active that results in the formation of a mixture having a melting point that is at least about 5° C. lower than the melting point of silthiopham. It is more preferred that the melting point of the mixture be at least about 10° C., even more preferred at least about 15° C., and yet more preferred that it be at least about 20° C. lower than the melting point of silthiopham.

Tebuconazole and simeconazole have been found to be preferred melting point depressants. A mixture of silthiopham and tebuconazole has been found to be a eutectic mixture having a eutectic point at a temperature of about 60° C., which is significantly lower than the melting point of either silthiopham (m.p. about 86° C.–88° C.) or tebuconazole (m.p. about 105° C.). For further information about the physical properties of pesticides, see, e.g., *The Pesticide Manual*, 11$^{th}$ Ed., C. D. S. Tomlin, Ed., British Crop Protection Council, Farnham, Surry, UK (1997).

After the liquid composition that contains the agricultural actives is formed by using a non-aromatic solvent, or by using a melting point depressant, as described above, the composition is dispersed into small droplets. As used herein, the term "small droplets" means droplets having an average size of less than about 20%. Although any method may be used for dispersing the liquid composition into droplets, a commonly used method is to mix the organic liquid composition with a sufficient amount of an aqueous liquid to form a continuous phase, and to carry out the mixing at high rates of shear, such as may be applied by a high shear mixer or blender.

When the small droplets of the liquid composition are formed, it has been found that the size of the droplets is a function of the rate of shear that is applied to the liquids during mixing, the viscosity of the two liquid phases, and the presence, type and amount of a surfactant or emulsifier material.

Surfactant or emulsifier materials that have been found to be useful in the present method include Lomar D (a sodium salt of naphthalene sulfonic acid polymer, 81% (CAS No. 9084-06-4) sodium sulfate, 12.5%, and water, 6.5%; available from Cognis Corp.) and Sokolan CP 9 (sodium salt of maleic acid-olefin copolymer (CAS No. 127123-37-3) available from BASF, Parsippany, N.J.).

A preferred method of forming the shell that encloses the small liquid droplets is by an interfacial polymerization of monomers to form a polyurea shell around each droplet. A method for accomplishing this polymerization is to add one or more types of isocyanate monomers to the organic liquid composition. The organic liquid composition can then be dispersed in the aqueous phase. One or more polyamine monomers can then be added to the aqueous liquid in which the organic liquid composition is dispersed. The polyamines react with the isocyanates at the interfacial surface of the small droplets (the organic/aqueous interface) to form a solid polyurea shell that encloses the droplets.

The isocyanates that are useful in the present method include polyisocyanates that can react with polyamines to form polyurea. One or more polyisocyanates can be used. Polyisocyanates that are useful in the present invention are discussed in *Chemistry and Technology of Isocyanates*, Ulrich, H., John Wiley & Sons, New York, (1996).

Monomeric polyisocyanates include aliphatic, cycloaliphatic, araliphatic, aromatic, and heterocyclic polyisocyanates. Examples of such polyisocyanates include 1,12-dodecane diisocyanate cyclobutane-1,3-diisocyanate, cyclohexane-1,3-diisocyanate, 2,4- and/or 2,6-hexahydrotoluylene diisocyanate, 4,4',4''-triphenylmethane triisocyanate, tris-(4-isocyanatophenyl)-thiophosphate, Desmodur N3300 with a CA registration No: 104559-01-5, (1,6-diisocyanate homo-polymer, available from Bayer Corporation, Pittsburgh, Pa.), OCN—R—(O—$CH_2CH_2$)$_x$—R—NCO (polyethylene glycol), OCN—R—(O$CH_2$—CH—$CH_3$)$_x$—R—NCO (polypropylene glycol), OCN—R—(O$CH_2CH_2CH_2CH_2$)$_x$—R—NCO (polytetramethylene glycol), OCN—R—(O$CH_2CH_2$OCO—$CH_2CH_2CH_2CH_2$—CO)$_x$—R—NCO (polyethyleneadipate), OCN—R—(O$CH_2CH_2CH_2CH_2$OCO—$CH_2CH_2CH_2CH_2$—CO)$_x$—R—NCO (polybutyleneadipate), and OCN—R—(O$CH_2CH_2CH_2CH_2CH_2CH_2$OCO)$_x$—R—NCO (polyhexamethylene-polycarbonate), where in each case, R can be $CH_2$ or $CH_2CH_2$ or alkyl.

It is preferred that the one or more polyisocyanates include at least one diisocyanate (having two reactive isocyanate groups per molecule) and/or at least one triisocyanate (having three reactive isocyanate groups per molecule).

Examples of useful diisocyanates can be found in the text by Ulrich, Id. at pp. 319, 330, 370, 374, and include (with commercial suppliers) HDI (Bayer), 1,5 Diisocyanatopentane, TMDI (Hüls), $C_{12}$DI (duPont), 1,6,11-Undecanetriioscyanate (duPont), CHDI (Akzo), BDI (Eastman/Sun), HXDI (Takeda), IPDI (BASF, Bayer, Hüls, Olin), IMCI, DDI-1410 (Henkel), XDI (Takeda), m-TMXDI (American Cyanamid), p-TMXDI (American Cyanamid), DEBI, HMDI (Bayer), OCN($CH_2$)$_3$O($CH_2$)$_3$NCO, OCN($CH_2$)$_3$O$CH_2CH_2$O($CH_2$)$_3$NCO, OCN($CH_2$)3O$CH$(CH3)$CH2$O(CH2)3NCO, OCN($CH_2$)$_3$O($CH_2$)$_3$O($CH_2$)$_3$NCO, OCN($CH_2$)$_3$O($CH_2$)$_2$O($CH_2$)$_2$O($CH_2$)$_3$NCO, OCN($CH_2$)$_3$OCH($CH_3$)CH($CH_3$)O($CH_2$)$_3$NCO, OCN($CH_2$)$_3$O$CH_2$C($CH_3$)$_2$$CH_2$O($CH_2$)$_3$NCO, OCN($CH_2$)$_3$O$CH_2$C(Et)$_2$$CH_2$O($CH_2$)$_3$NCO,

OCN($CH_2$)$_3$O$CH_2$C($C_3H_7$)$CH_2$O($CH_2$)$_3$NCO,
      |
      $CH_3$

OCN($CH_2$)$_3$O($CH_2$)$_4$O($CH_2$)$_3$NCO, OCN($CH_2$)$_3$O($CH_2$)$_6$O($CH_2$)$_3$NCO, OCN($CH_2$)$_3$O($CH_2$)$_{10}$O($CH_2$)$_3$NCO, PPDI (Akzo, duPont), 2,4-TDI (Bayer), TDI(80:20) (BASF, Dow, Olin, Rhone-Poulenc, Enichem), MDI (BASF, Bayer, Dow, ICI, Enichem, Mitsui, Toatsu), PMDI (BASF, Bayer, Dow, ICI, Enichem, Mitsui, Toatsu), NDI (Bayer), TODI (Nippon-Soda), and the like.

Blends of of diisocyanates and triisocyanates that are useful in the present invention are disclosed in U.S. Pat. No. 5,925,595, to Seitz et al. A preferred diisocyanate is meta-tetramethylenexylylene diisocyanate (TMXDI), and a preferred triisocyanate is N,N',N''-tris(6-isocyanatohexyl)-nitrodotricarbonic triamide (CAS N. 67635-83-0; available as Desmodur N3,200 from Bayer Corporation, Pittsburgh, Pa.). It is more preferred that the polyisocyanates include both a diisocyanate and a triisocyanate.

It is believed that the ratio between the number of functional groups supplied by the diisocyanate and by the triisocyanate has an effect upon the composition of the polyurea shell and, thus, can be used as a controllable parameter for obtaining a desired release rate. When TMXDI and N,N',N''-tris(6-isocyanatohexyl)-nitrodotricarbonic triamide are used as the diisocyanate and triisocyanate, respectively, a preferred ratio is 1:1.

Polyamines (i.e., polyfunctional amines) that are useful in the present method include any polyamine that is capable of reacting with polyisocyanates to form polyurea. Suitable amines include, but are not limited to, diethylene triamine, triethylene tetramine, tetraethylene pentamine, iminobispropylamines, amine epoxy adducts, alkyldiamines from ethylene diamine to hexamethylene diamine, trimethylolpropane tris[poly(propylene glycol)amine terminated] ether (available as Jeffamine T-403, CAS No. 39423-51-3) from Texaco Corp. or Aldrich), all diamines and triamines produced by Texaco Corp. and marketed under the trade name of Jeffamine, piperazine, isophorone diamine, bis-(4-aminocyclohexyl)methane, 1,2-, 1,3-, and 1,4-cyclohexane diamine, 1,2-propane diamine, N,N,N-tris-(2-aminoethyl)-amine, poly(ethyleneimine)s, N-(2-aminoethyl)-piperazine, N,N'-bis-(3-aminopropyl)-ethylenediamine, N,N'-bis-(2-aminoethyl)-1,3-propylenediamine, N,N'-bis-(3-aminopropyl)-1,3-propylenediamine, N,N,N'-tri-(2-aminoethyl)-ethylene diamine, It is preferred that the one or more polyamines that are used in the method include at least one triamine and/or at least one tetramine. In fact, it is more preferred that two or more polyamines be used and that they be selected from diamines, triamines and tetramines. It is even more preferred that both a triamine and a tetramine are included. Preferred triamines include trimethylolpropane tris[poly(propylene glycol)amine terminated]ether (available as Jeffamine T-403), and diethylene triamine, and preferred tetramines include triethylenetetramine (TETA).

When a blend of a triamine and a tetramine is added to the reaction, it is preferred that the ratio of the number of functional groups supplied by the triamine relative to the number of functional groups supplied by the tetramine that is used is between about 100:0 to 0:100. As used herein, this ratio may be referred to as the ratio between the of equivalents of triamine:tetramine. A ratio of equivalents of triamine:tetramine of between about 90:10 and 10:90 is more preferred, yet more preferred is a ratio of between about 80:20 and 20:80, even more preferred is a ratio of between about 60:40 and 40:60, and yet more preferred is a ratio of about 50:50.

It has been found that the release rate of an agricultural active in the core of a microparticle having a polyurea shell, can be modulated by varying the ratio of the equivalents of a triamine such as Jeffamine T-403 and the equivalents of a tetramine such as triethylene tetramine. Accordingly, the parameter of the equivalents ratio of triamine to tetramine that is used in the interfacial polymerization reaction is one of the parameters that can be used to obtain a pre-selected controlled release rate of the active.

When the total amount of polyisocyanates and the total amount of polyamines that are contacted in the present method are considered, it is preferred that the ratio of the total equivalents of polyisocyanates to the total equivalents of polyamines is between about 4:1 and 1:4, more preferred is a ratio of 2:1 to 1:2, and yet more preferred is a ratio of about 1:1.

It is believed that the temperature at which the polymerization reaction takes place is a factor in obtaining a fully-formed and intact shell, without pores or other significant irregularities. Accordingly, it is preferred that the polymerization reaction is carried out at a temperature of between about 25° C. and about 90° C., and more preferred that the temperature be between about 40° C. and 75° C.

When the novel microcapsules are formed, the thickness of the shell wall can be controlled by varying the amount of the combined polyisocyanates and polyamines that are used, relative to the total amount of the liquid organic phase. The higher the level of polyisocyanates and polyamines with respect to the amount of the liquid organic phase, the thicker the polyurea shell wall that will be formed. In this specification the shell wall thickness is expressed in terms of the weight ratio of polyurea to core material. The weight ratio of the polyurea shell to the core can be controlled as described above, and desirably falls between about 5:100 and about 50:100. It is more preferred that the shell:core weight ratio is between about 10:100 and about 40:100, yet more preferred about 15:100 to about 30:100. However, since the thickness of the shell wall has an effect on the rate of release of an agricultural active from the core of the microcapsule when it is exposed to natural environmental conditions, shell wall thickness is a variable that can be controlled to provide a pre-selected release rate profile.

The terms "natural environmental conditions", as used herein, are to be understood to mean the weather conditions that a microcapsule of the present invention will be exposed to when it is applied to a plant, a seed, or to soil, in a conventional soil-based growing environment. Such conditions include normal ambient rainfall, soil moisture, sunshine, temperature, biological activity, and the like.

When it is said that the agricultural active is released from the microcapsule at a "pre-selected controlled rate", the terms "pre-selected controlled rate" refer to a pre-selected release profile of the active from the microcapsules, as can be represented by a plot of the cumulative amount of the active that has been released as a function of the time of exposure. One method of obtaining a microcapsule having a pre-selected controlled release rate is to determine the release rate of the active from the microcapsule under standardized test conditions (such as are described in detail in the Examples below) and then correlating the release profile obtained under standard conditions with the release profile of the active under normal environmental conditions. One of skill in the art of controlled released pesticides would understand that after this correlation is made several times, the release profile determined according to the standardized test methods can be used to predict the release rate under normal environmental conditions.

The controlled release forms of the present invention can be of any geometrical shape, but spherical microcapsules are preferred. A particularly useful form of the novel microcapsule includes a polyurea shell enclosing a core which comprises silthiopham, where the microcapsule has an average size of from about $2\mu$ to about $8\mu$ where the weight ratio of the shell to the core is from about 15:100 to about 30:100, and where the amount of silthiopham in the core is from about 30% to about 60%, by weight.

The microcapsules can be used in any manner in which other controlled release forms of agricultural actives are used, and can be applied to the soil, to seeds, roots, tubers, and any other form of plant propagation material, as well as to any part of a growing plant. The subject microcapsules can be used, without limitation, on such plants as corn, cereals, including wheat, barley, rye, and rice, vegetables, clovers, legumes, including beans, peas and alfalfa, vegetables, sugar cane, sugar beets, tobacco, cotton, rapeseed, sunflower, safflower, and sorghum, and on plant propagation material of such plants.

It is preferred that the microcapsules be used with legumes (members of the class Magnoliopsida and the order Fabales). It is more preferred that the plant be in the family Fabaceae (formerly Leguminosae) and the sub-family Papilionoideae or Faboideae, and even more preferred that the plant be selected from the group consisting of *Pisum* spp. (including the garden pea, *P. sativum*), *Medicago* spp. (including alfalfa, *M. sativa*), *Arachis* spp. (including peanuts, *A. hypogaea*), soybeans (including *Glycine max, Glycine hispida*), *Vicia* spp. (including vetches), *Vigna* spp. (including cowpeans), *Vicia* spp. (including fava bean, *V. faba*), trefoil, clovers and *Phaseolus* spp. (including *P. vulgaris, P. lunatus, P. limensis*, and *P. coccineus*). It is most preferred that the present microcapsules be used with wheat and soybeans.

The microcapsules can be applied to any type of plant seed as a coating, either neat or with sticking agents or other adjuvants.

When silthiopham is used as the first agricultural active, a preferred application is to apply the controlled release microcapsules to the seeds or the soil during the planting of winter wheat in order to obtain protective activity against *Gaeumannomyces graminis* in the fall and throughout the winter, but to retain sufficient activity to provide protection against renewed biological challenge in the spring.

In those embodiments of the invention where the high melting material is other than an agricultural active, the same general techniques, times, temperatures and concentrations can be used for the preparation of microcapsules that have been described herein for agricultural actives.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples. In the examples all percentages are given on a weight basis unless otherwise indicated.

EXAMPLE 1

This example illustrates the production of microcapsules containing silthiopham as the agricultural active and with the use of a citric acid derivative as an organic solvent.

An aqueous solution of Lomar D surfactant (5.16 g; available from Henkel Corp., Morristown, N.J.) was prepared in 90.4 g water in a 250 ml beaker. The pH of the solution was adjusted to 7.2 by adding a small amount of citric acid, and the solution was heated to 55° C. An organic liquid solution was prepared by intermixing silthiopham (N-allyl-4,5-dimethyl-2-trimethylsilylthiophene-3-carboxamide, 16.00 g, available from Monsanto Company, St. Louis, Mo.), acetyltri-n-butyl-citrate (34.0 g; available as Citroflex A-4 from Morflex, Inc., Greensboro, N.C.), Desmodur N 3,200 (7.23 g; an aliphatic polyisocyanate (tri-isocyanate) based on hexamethylene diisocyanate, available from Bayer Corporation, Pittsburgh, Pa.) and meta-tetramethylenexylylene diisocyanate (TMXDI) (2.37 g; available from Miles Laboratories, Inc.) and then heating the mixture until all of the solids were dissolved. While the temperature of the solution was maintained at 50–55° C., the solution was agitated with a Silverson S4RT-4 mixer equipped with a six hole screen for 5–10 seconds at 4,200 rpm and the organic solution was added into the agitated solution in 20 seconds. The mixture was further agitated at 9,500 to 10,200 rpm for 40 seconds. After the formed emulsion was transferred into a 400 ml beaker equipped with a mechanic stirrer set at 625 rpm, an amine solution containing water (5.38 g), triethylenetetramine (m.w. 146.2), (1.10 g) and trimethylolpropane tris[poly(propylene glycol) amine terminated]ether (4.32 g, available as Jeffamine T-403, from Texaco Co. or Aldrich; m.w. ~440) was added into the emulsion immediately. The temperature of the beaker was maintained at 55°–62° C. for 3 hours after which most of the isocyanate infrared absorbance peak at 2270 $cm^{-1}$ had disappeared—indicating reaction of the isocyanate. A light yellow slurry (118 g) was collected. The average particle size was 4.2 microns. The weight ratio between wall and core was 30:100 and the amount of silthiopham in the core was 32% by weight.

EXAMPLE 2

This example illustrates the production of microcapsules containing silthiopham having thinner shells than in Example 1.

An aqueous solution of Lomar D (5.16 g) was added to 90.4 g water in a 250 ml beaker, and the pH of the solution was adjusted to 7.2 by adding a small amount of citric acid and the solution was heated to 55° C. An organic solution was prepared by intermixing silthiopham (16.00 g), Citroflex A-4 (34.0 g), Desmodur N 3,200 (4.82 g) and TMXDI (1.58 g) and then heating the mixture until all of the solids dissolved and the temperature of the solution was maintained at 50°–55° C. The aqueous solution was agitated with a Silverson S4RT-4 mixer equipped with a six hole screen for 5–10 seconds at 4,200 rpm and the organic solution was added to the agitated solution in 20 seconds. The mixture was further agitated at 9,500 to 10,200 rpm for 40 seconds. After the formed emulsion was transferred into a 400 ml beaker equipped with a mechanic stirrer set at 625 rpm, an amine solution containing water (5.38 g), triethylenetetramine (0.73 g) and Jeffamine T403 (2.88 g) was added into the emulsion immediately. The temperature of the beaker was remained at 55°–62° C. for 2 hours. The isocyanate infrared absorbance peak at 2270 $cm^{-1}$ disappeared. 114 g of light yellow slurry was collected. The average particle size was 4.21 micron. The weight ratio between wall and core of the particles was 20:100 and the amount of active in the core was 32% by weight.

EXAMPLE 3

This illustrates the formation of microcapsules containing a higher level of silthiopham in the core.

An aqueous solution of Lomar D (5.16 g) was prepared by adding the surfactant to 90.4 g water in a 250 ml beaker. The pH of the solution was adjusted to 7.2 by adding a small amount of citric acid and heated to 55° C. An organic solution was prepared by mixing silthiopham (16.00 g), Citroflex A-4 (34.0 g), Desmodur N 3,200 (7.23 g) and TMXDI (2.37 g) together and then heating the mixture until all of the solids were dissolved and the temperature of the solution was maintained at 50°–55° C. The aqueous solution was agitated with a Silverson S4RT-4 mixer equipped with a six hole screen for 5–10 seconds at 4,200 rpm and the organic solution was added into the agitated solution in 20 seconds. The mixture was further agitated at 9,500 to 10,200 rpm for 40 seconds. After the formed emulsion was transferred into a 400 ml beaker equipped with a mechanic stirrer set at 625 rpm, an amine solution containing water (5.38 g), triethylenetetramine (1.10 g) and Jeffamine T-403 (4.32 g) was added into the emulsion immediately. The temperature of the beaker was remained at 55°–62° C. for 3 hours. Most of the isocyanate infrared absorbance peak at 2270 $cm^{-1}$ disappeared. 118 g of light yellow slurry was collected. The average particle size was 4.2 micron. The weight ratio between wall and core was 30:100 and the amount of active in the core was 40% by weight.

EXAMPLE 4

This illustrates the preparation of microcapsules containing silthiopham having 20:100 wall:core weight ratio and 40% by weight active in the core.

An aqueous solution of Lomar D (5.16 g) was prepared by adding the surfactant to 90.4 g water in a 250 ml beaker. The pH of the solution was adjusted to 7.2 by adding a small amount of citric acid and the solution was heated to 55° C. An organic solution was prepared by mixing silthiopham (20.00 g), Citroflex A-4 (30.0 g), Desmodur N 3,200 (4.64 g) and TMXDI (1.74 g) together and then heating the mixture until all of the solids were dissolved and the temperature of the solution was maintained at 50°–55° C. The aqueous solution was agitated with a Silverson S4RT-4 mixer equipped with a six hole screen for 5–10 seconds at 4,200 rpm and the organic solution was added into the agitated solution in 20 seconds. The mixture was further agitated at 9,500 to 10,200 rpm for 40 seconds. After the formed emulsion was transferred into a 400 ml beaker equipped with a mechanic stirrer set at 625 rpm, an amine solution containing water (4.00 g), triethylenetetramine (0.74 g) and Jeffamine T-403 (2.90 g) was added into the emulsion immediately. The temperature of the beaker was maintained at 55°–62° C. for 2.5 hours. The isocyanate infrared absorbance peak at 2270 $cm^{-1}$ disappeared. 118 g of light yellow slurry was collected. The average particle size was 4.5 micron. The weight ratio between the wall and core was 20:100 and the amount of active in the core was 40%.

EXAMPLE 5

This illustrates the production of microcapsules containing silthiopham where the capsules have a 15:100 weight ratio of wall:core.

Microcapsules were produced by the method described in Example 4, except that the organic solution contained 3.61 g of Desmodur N 3,200 and 1.19 g of TMXDI, and the amine solution contained 3.0 g of water, 0.55 g of triethylenetetramine and 2.16 g of Jeffamine T-403. 107 g of a light yellow product was collected and the average particle size was 3.4 microns. The weight ratio between the wall and the core was 15:100 and the amount of silthiopham in the core was 40% by weight.

EXAMPLE 6

This illustrates the effect of the wall thickness of microcapsules on the release rate of silthiopham into water.

Microcapsules containing silthiopham were produced by the method described in Examples 3–5, except that the ratio of equivalents of Desmodur N3,200 and TMXDI was maintained at 2:1, and the ratio of total isocyanate functional groups to total amine functional groups was maintained at 1:1 so that the polymerization reaction was stoichiometrically balanced. Microcapsules having wall:core weight ratios of 15:100, 20:100 and 30:100 were then prepared, and the properties of these microcapsules are shown in Table 1. The release rate of silthiopham was measured as described below.

TABLE 1

Properties of microcroencapsulated silthiopham.

| Sample | Wall:Core Weight Ratio | Ratio of TETA:T-403[a] | Avg. Particle size (microns) | % REA |
|---|---|---|---|---|
| 1 | 15:100 | 50:50 | 3.5 μ | 1.5% |
| 2 | 20:100 | 50:50 | 3.7 μ | 1.2% |
| 3 | 30:100 | 50:50 | 4.5 μ | 0.5% |

Notes:
[a]Ratio of TETA:T-403 is equivalents of TETA:equivalents of T-403.

The release rate of an agricultural active from a controlled release formulation was measured by placing the controlled release formulation in a water sink so that at 100% release the total active present is less than approximately one third the water solubility level. The release solution is then agitated by shaking or stirring. At intervals, an aliquot is removed. The aliquot is filtered to separate the controlled release matrix from active dissolved in water. The filtered aliquot is then assayed for active present. Release curves are plotted to show hours after start of experiment vs percent of total active released.

When the release rate of microcapsules having a polyurea shell, or wall, enclosing a core containing silthiopham was tested, the following procedure was followed:

Release Solution Preparation:
Prepare 450 mL of a solution of the formulation containing a target of 10–12 ppm silthiopham (silthiopham water solubility is 35 ppm at 20° C.).
Note time of start.
Immediately invert solution approximately 100 times and take an aliquot.
Agitate by shaking on a platform shaker.
Separation of Dissolved Active from Controlled Release Matrix:
Notetime.
Take an aliquot immediately after shaking (the level of active in this sample is reported as the percentage of readily extractable active (% REA), which is believed to represent the relative amount of active that was not enclosed in the microcapsules, or was present on the surface of the microcapsules).
Filter with a 0.45 micron PTFE filter—discarding first 3 mL.
Assay filtered aliquot by HPLC.
HPLC Methodology (Reverse Phase; UV):

| Column: | Alltech Alltima C18; 5 micron particle size; (250 × 4.5 mm) |
|---|---|
| Flow: | 1.2 mL/min |
| Injection volume: | 100 microliters |
| Detector: | UV; 220 nanometers (Varian 9050) |
| Mobile phase A: | 12.6 g K$_2$HPO$_4$ + 3600 mL water to pH 6.4 with 85% H$_3$PO$_4$. Add 400 mL methanol. |
| Mobile phase B: | Methanol |
| Mobile phase: | 22% A; 78% B |
| Approximate retention time: | 6 to 7 minutes |
| Standard range: | 0.15 to 15 ppm silthiopham. |

Release rates of the microcapsule products of Samples 1–3 were measured as described above and the results are shown in FIG. 1. As can be seen, less than 10% of the silthiopham was released from sample 3 (having 30:100 wall:core ratio) after 1,500 hours, and the release rate increased as the wall:core ratio (essentially a measure of the thickness of the polyurea shell) decreased. This showed that the release rate could be modulated by controlling the wall:core ratio and that almost all of the active was present in the cores of the microcapsules. It was observed, however, that the release rate of each of the three samples was relatively low.

Figure 2:
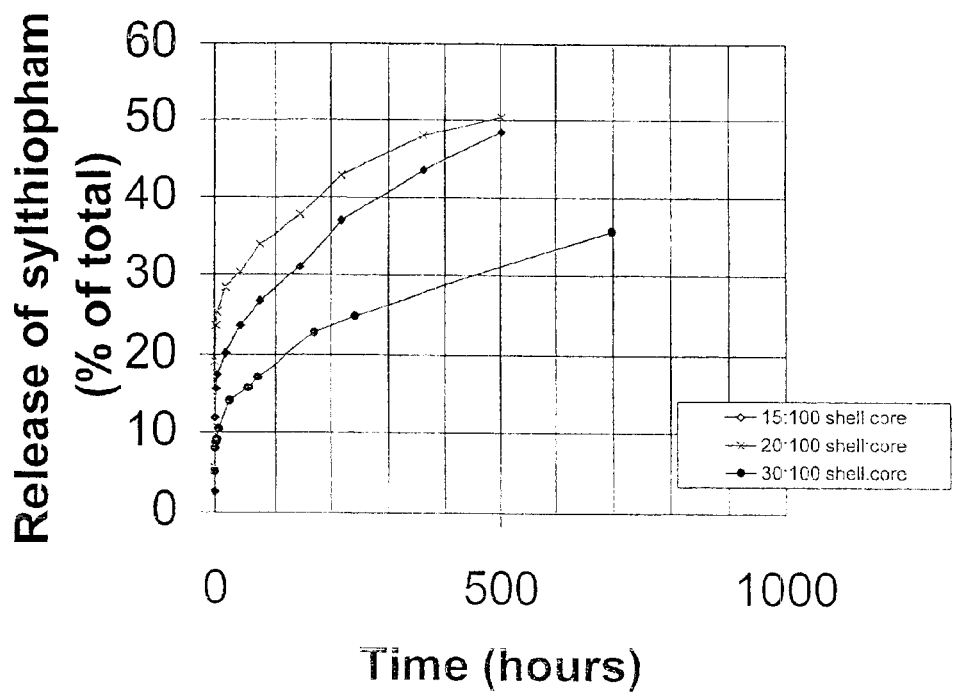
FIG. 2 shows a release rate profile showing the release of silthiopham as a function of time and as a function of shell wall thickness for microcapsules having 50% silthiopham in the core, where profiles are shown for microcapsules having shell:core weight ratios of 15:100, 20:100, and 30:100.
Figure 3:
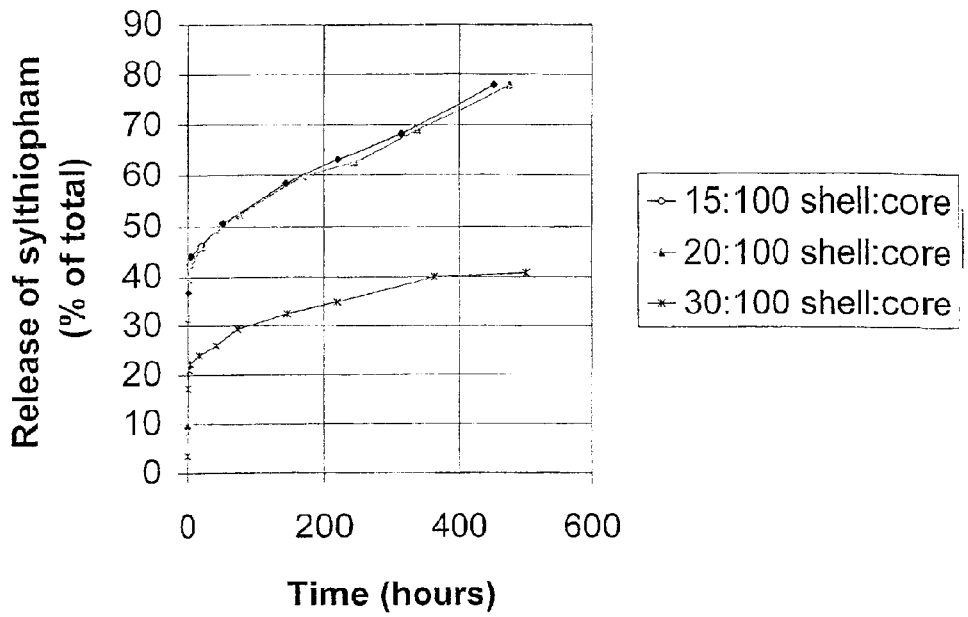
FIG. 3 shows a release rate profile showing the release of silthiopham as a function of time and as a function of shell wall thickness for microcapsules having 60% silthiopham in the core, where profiles are shown for microcapsules having shell:core weight ratios of 15:100, 20:100, and 30:100.

Microcapsules were prepared by the same methods as described in Examples 3–5, except that the amount of silthiopham that was loaded into the core was varied to provide silthiopham loadings of 50% and 60%, by weight, of the core. The wall:core ratio for the microcapsules was varied from 15:100, 20:100 and 30:100, as described above in Example 6. The release rates of each of the microcapsules having different silthiopham loading rates were measured and the results are shown in FIG. 2 for the 50% loading, and FIG. 3 for the 60% loading. In general, it can be seen that the higher the active loading in the core, the more rapid the release rate, while thicker shell walls give lower release rates, as would be expected.

EXAMPLE 7

This illustrates the effect of the amount of active in the core of the microcapsules on the release rate of silthiopham into water.

Microcapsules containing silthiopham were produced by the method described in Example 6, except that the wall:core ratio was maintained at 30:100, while the loading of silthiopham in the core was varied from 32% to 60%, by weight. Also, the reaction mixture was intermixed by the use of a Waring blender, rather than with a Silverson mixer. When the Waring blender was used, it was found that, in general, smaller microcapsules could be formed than when the Silverson mixer was used.

A 500 ml Waring blender was connected to a 0–140 volt Variac voltage controller to provide speed control. The aqueous solution was placed in the blender and mixed at a Variac setting of 30/140 V during the addition of the organic solution—over a period of about 20 seconds. After the organic solution had been added, the Variac was increased to 140/140 V to provide maximum speed for 40 seconds. The speed was then reduced to a 20/140 V Variac setting for the addition of the amine mixture. This took approximately one minute, after which the mixture was immediately transferred to a beaker being stirred at about 250–450 rpm by an overhead stirrer for the duration of the reaction.

The properties of the microcapsules are shown in Table 2.

TABLE 2

Properties of microcapsules containing slithiopham.

| Sample | Amount of Active in core (% by weight) | Ratio of TETA:T-403[a] | Avg. Particle size (microns) | % REA |
|---|---|---|---|---|
| 4 | 32% | 50:50 | 2.4 μ | 1.4% |
| 5 | 50% | 50:50 | 2.4 μ | 5.0% |
| 6 | 60% | 50:50 | 2.2 μ | 3.8% |

Notes:
[a]Ratio of TETA:T-403 is equivalents of TETA to equivalents of T-403.

Figure 4:
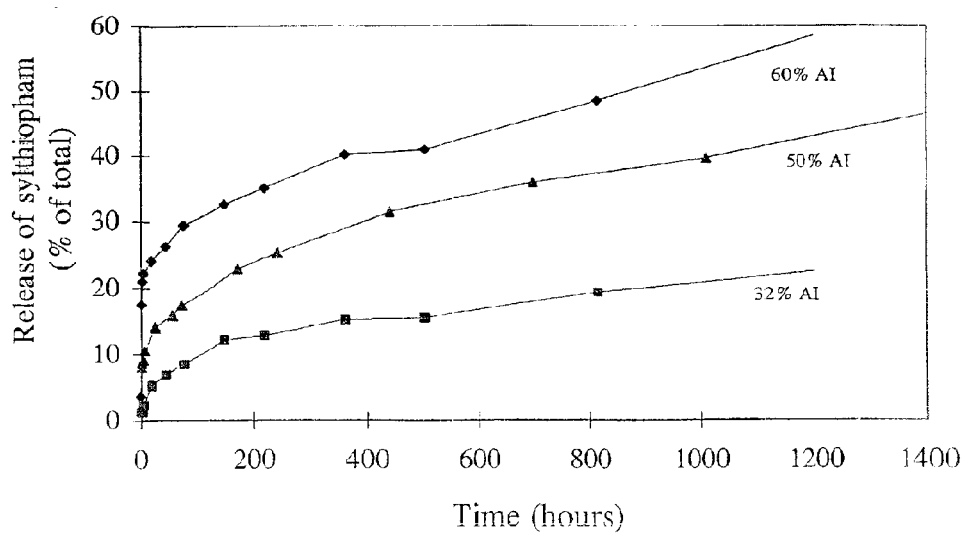
FIG. 4 shows release rate profiles for the release of silthiopham from microcapsules having a shell:core ratio of 30:100, where release profiles are shown as a function of the amount of silthiopham originally in the core.

The release rate of silthiopham from the microcapsules was measured as described in Example 6, and the results are shown in FIG. 4. It is seen there that the sample having the highest level of silthiopham in the core provided the fastest release rate, with release rate decreasing as the level of silthiopham in the core decreased. All microcapsules were still releasing after 1,200 hours (50 days). This showed that the release rate could be modulated by controlling the amount of active initially placed in the core of the microcapsules.

Figure 5:
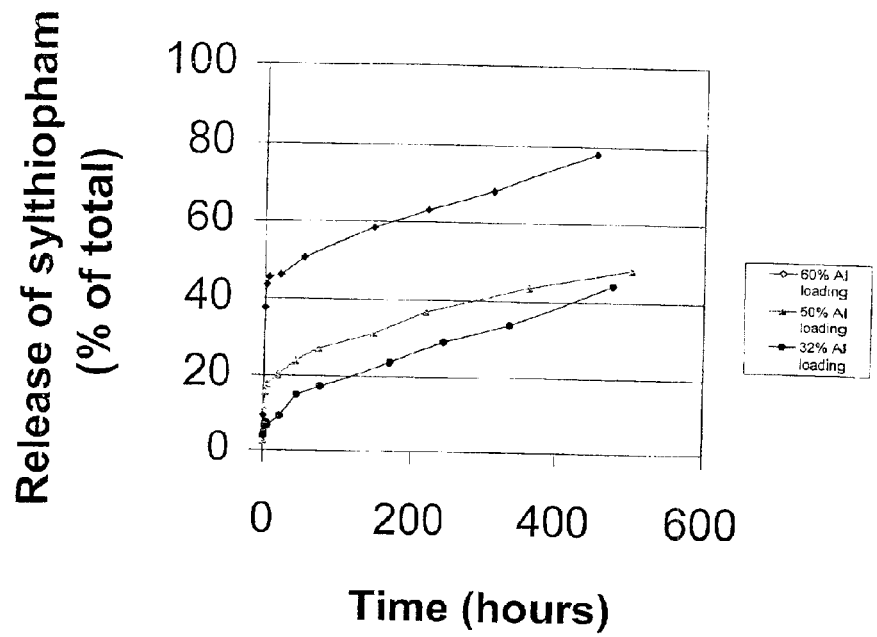
FIG. 5 shows release rate profiles for the release of silthiopham from microcapsules having a shell:core ratio of 15:100, where release profiles are shown as a function of the amount of silthiopham originally in the core.
Figure 6:
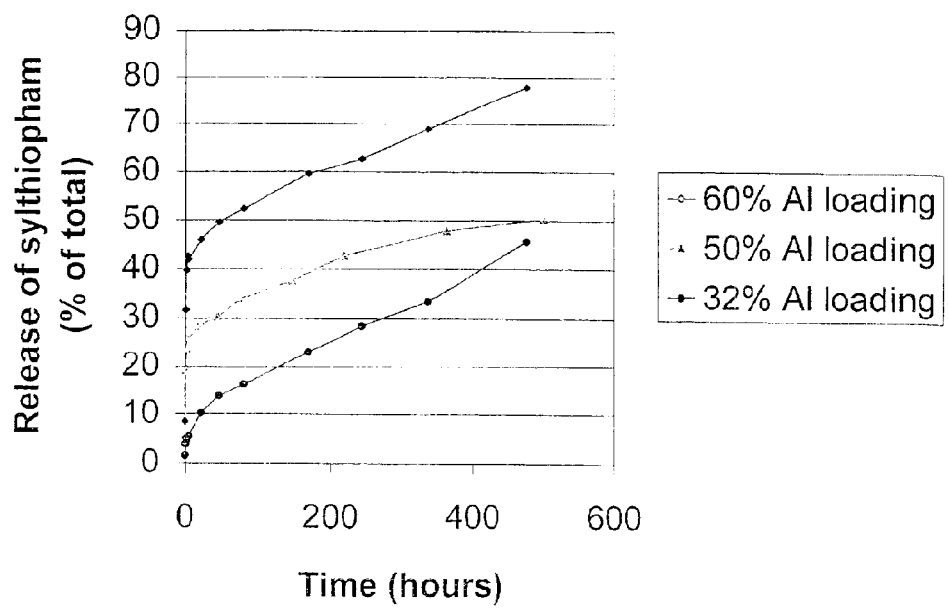
FIG. 6 shows release rate profiles for the release of silthiopham from microcapsules having a shell:core ratio of 20:100, where release profiles are shown as a function of the amount of silthiopham originally in the core.

Microcapsules having 15:100 and 20:100 shell:core ratios were also produced by the same methods and each had silthiopham loadings of 32%, 50% and 60% by weight in the core. Release rates for these samples were also measured as described in Example 6, and the results are shown in FIG. 5 for microcapsules having 15:100 shell:core ratio and in FIG. 6 for 20:100 shell:core ratio. It can be seen that the release rate can be modulated by varying the shell:core ratio and by varying the loading of the active in the core. In general, the thicker the shell wall, the slower the release rate, while the higher the loading of active in the core, the faster the release rate.

EXAMPLE 8

This example illustrates the effect of particle size on the release rate of silthiopham from microcapsules having polyurea shells.

Figure 7:
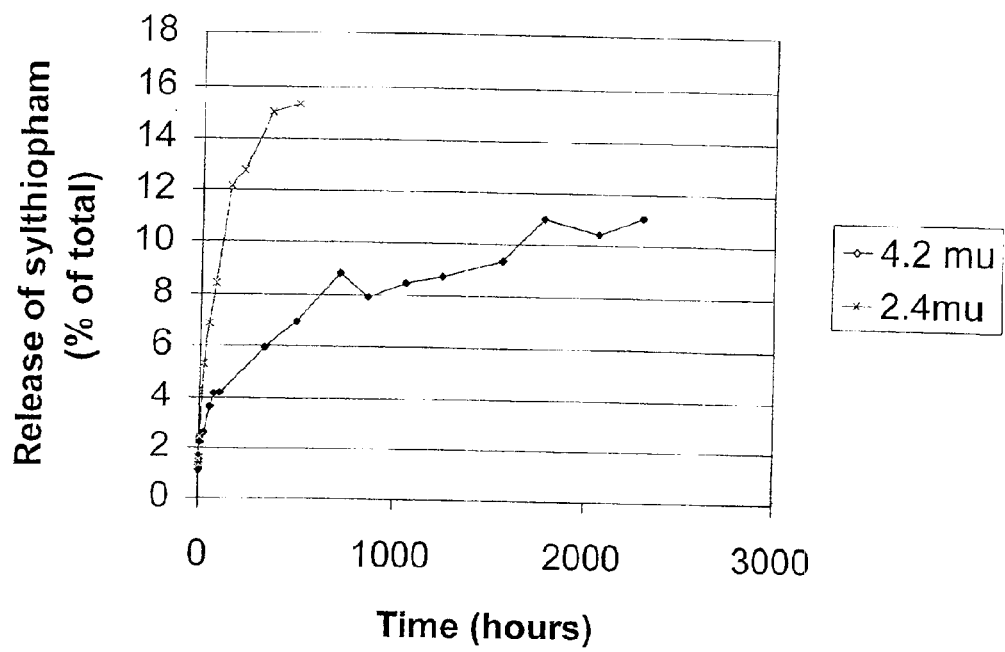
FIG. 7 illustrates the effect of particle size on the release profiles for the release of silthiopham from microcapsules having a shell:core ratio of 30:100, for microcapsules having an average size of 2.4µ and 4.2µ.
Figure 8:
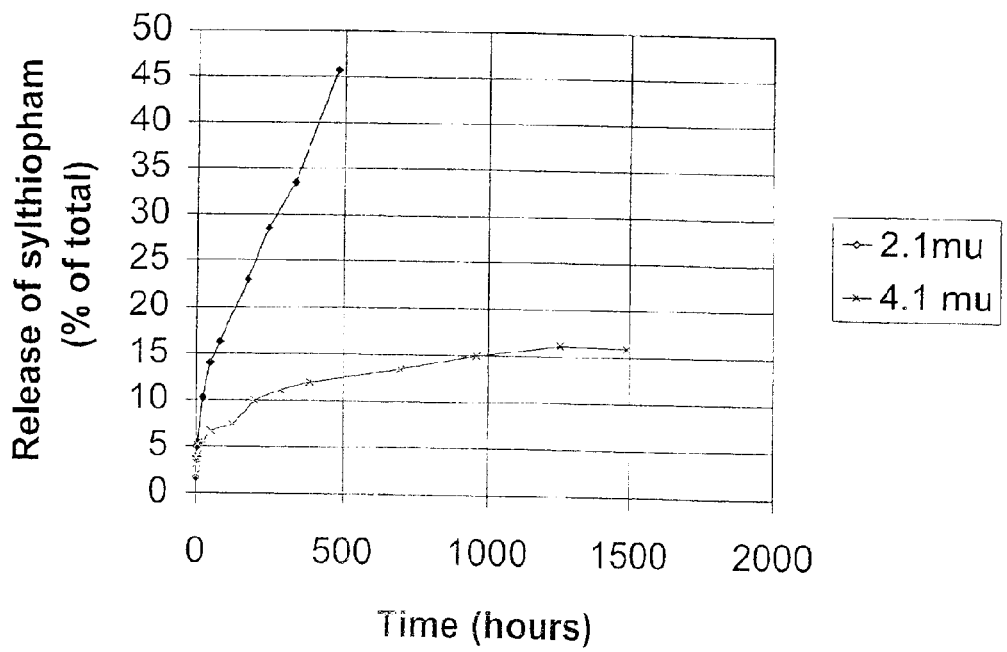
FIG. 8 illustrates the effect of particle size on the release profiles for the release of silthiopham from microcapsules having a shell:core ratio of 20:100 and having a 32% by weight loading of silthiopham in the core, for microcapsules having an average size of 2.1µ and 4.1µ.

Microcapsules were prepared by the methods described in Example 6, except that the wall:core ratio was maintained at 30:100 and the loading of silthiopham in the core was maintained at 32% by weight. The average particle size was varied from 2.4μ (Sample 7—processed in a Waring blender as in Example 7) to 4.2μ (Sample 8—processed by a Silverson mixer as in Example 1). The release rate of silthiopham was measured as described in Example 6, and the results are shown in FIG. 7. As can be seen from that figure, as the microcapsule size increases, the release rate decreases. It was also seen that the initial release rate was higher for the smaller particles (5% REA for the 2.4μ particles versus less than 1% REA for the 4.2μ particles). This test was repeated for microcapsules that were formed by the same method, but had a shell:core ratio of 20:100, 32% loading of silthiopham in the core, and particle sizes of 2.1μ and 4.1%. Release rates of silthiopham were measured for these particles by the same methods and the release curves are shown in FIG. 8.

The data from both curves shows that the release rate of the active can be modulated by controlling the size of the microcapsule. It is believed that size can be controlled by, for example, control on the shear severity and duration during blending of the aqueous and organic phase liquid, and by controlling the temperature and the viscosity of the two phases. It is believed that microcapsules between about 2μ and about 8μ are preferred for the present applications, although both larger and smaller microcapsules are possible.

EXAMPLE 9

This example illustrates the effect of the composition of the shell wall on the release rate of silthiopham from microcapsules having polyurea shells.

Figure 9:
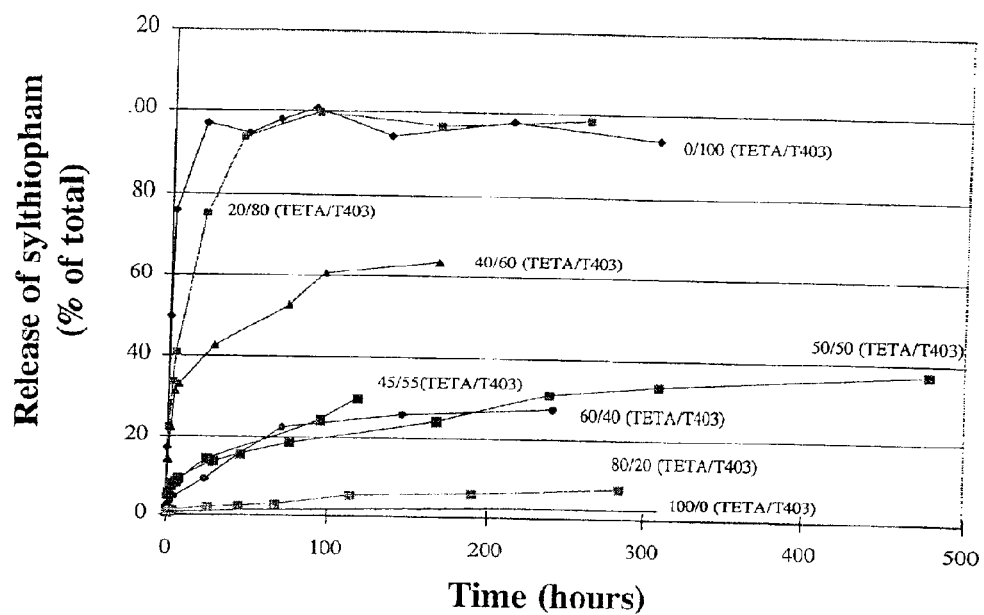
FIG. 9 illustrates the effect on silthiopham release rate of the ratio of triethylene tetramine (TETA)-to-Jeffamine T-403 (T-403, a tri-functional amine) that was used in the interfacial polymerization to form a polyurea shell for microcapsules having a shell:core weight ratio of 20:100, and shows the release profiles for the release of silthiopham for microcapsules produced with TETA/T-403 ratios ranging from 0/100 to 100/0.

In this set of experiments, microcapsules were produced by the methods described in Example 6, except that the wall:core weight ratio was maintained at 20:100 and the loading of silthiopham in the core was maintained at 50% while the amount of Jeffamine T-403 used in the reaction was increased from 0 to 100%, and a Waring blender was used for mixing as described in Example 7. Properties of the resulting microcapsules are summarized in Table 3. The average particle size for all of the samples ranged from 2.2 to 2.4 microns, which indicated that the ratio of TETA and Jeffamine T-403 did not significantly effect the average particle size. In fact, the average particle size of the microcapsule was found to depend on (1) the agitation during blending of the aqueous and organic liquids, (2) the viscosity of the dispersed or emulsified organic phase which contains the active, the solvent, and the isocyanates and (3) the emulsifier or the dispersion reagent. The initial release is associated with the composition of the shell. As can be seen from the data in Table 3, the initial release remained at 0.6% level when the ratio between the equivalents of TETA and the equivalents of Jeffamine T-403 was below 50%/50%. However the initial release of silthiopham was increased from 1.4% to even 17% when the ratio between TETA and Jeffamine T-403 was decreased from 50%/50% to 0/100%. This result agrees with the release profiles of silthiopham in water, which are shown in FIG. 9 where it is seen that the release rate decreases when the concentration of TETA in the in the polymerization reaction increases, i.e., when the equivalents ratio between TETA and Jeffamine T-403 increases. When 100% of Jeffamine T-403 was used, silthiopham was released into water most rapidly. Whereas, when 100% of TETA was used, the release of silthiopham was extremely slow and less than 10% of silthiopham was released even after 300 hours. According to the chemical structures of both amines, the Jeffamine T-403 molecule with a molecular weight of 440 has three amine groups whereas TETA with a molecular weight of 162 has four amine groups.

Figure 10:
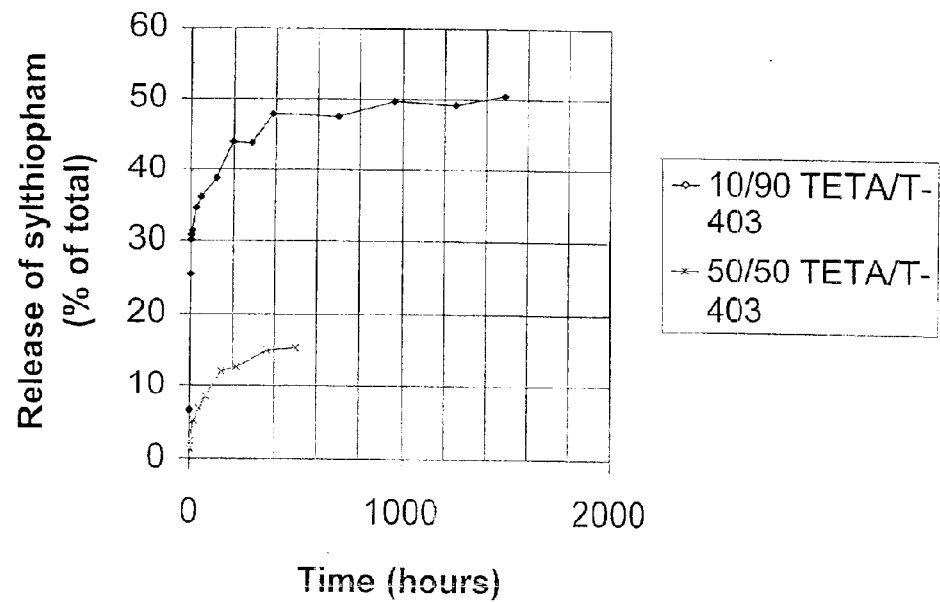
FIG. 10 illustrates the effect on silthiopham release rate of the ratio of triethylene tetramine (TETA)-to-Jeffamine T-403 (T-403, a tri-functional amine) that was used in the interfacial polymerization to form a polyurea shell for microcapsules having a shell:core weight ratio of 30:100, and shows the release profiles for the release of silthiopham for microcapsules produced with TETA/T-403 ratios of 10/90 and 50/50.

This experiment was repeated with microcapsules having shell:core ratios of 30:100, rather than 20:100, and the effect of varying the TETA/T-403 ratio on the release rate was found to be the same as for the thinner capsule wall. The release rate results for the microcapsules having a 30:100 shell:core ratio are shown in FIG. 10 for 10/90 and 50/50 TETA/T-403 ratios. As expected, the release rates for the thicker-wall microcapsules was slower than for the thinner wall capsules.

In general an amine group in the polyamine molecule will react with an isocyanate to give polyurea. In this process the reaction occurs at the interface of the organic droplet and the aqueous solution, and a shell composed of polyurea forms. It is believed that the density or the permeability of the shell will depend on the composition of the polyurea. Since TETA with four amine groups is a much smaller molecule than Jeffamine T-403 with three amine groups, it is believed that the polyurea shell made with higher TETA concentration will have the more condensed shell therefore provide slower release rate of silthiopham. Therefore, the results show that the release profiles of silthiopham in water can be controlled by varying the ratios of TETA and Jeffamine T-403 used during the polymerization.

TABLE 3

Properties of microencapsulated silthiopham.

| Sample | Wall Thickness | TETA/T403[a] | Particle Size | REA |
|---|---|---|---|---|
| 9 | 20% | 0/100% | 2.2 μ | 17% |
| 10 | 20% | 20%/80% | 2.2 μ | 4.9% |
| 11 | 20% | 40%/60% | 2.2 μ | 2.4% |
| 12 | 20% | 50%/50% | 2.4 μ | 1.4% |
| 13 | 20% | 60%/40% | 2.2 μ | 0.60% |
| 14 | 20% | 80%/20% | 2.3 μ | 0.50% |
| 15 | 20% | 100%/0% | 2.2 μ | 0.66% |

Notes:
[a]The ratio of TETA/T-403 is given as equivalents of TETA per equivalent of T-403.

EXAMPLE 10

This illustrates the stability of microencapsulated silthiopham.

The stability of the encapsulated silthiopham products was studied by measuring the initial release of silthiopham in the products after they had aged for a certain period after synthesis. As can be seen in Table 4, the stability of the microcapsules varies somewhat between microcapsules having different synthesis parameters, but is, in general, acceptable for a commercially useful product. The initial release of Sample 8 was slightly increased to 1.8% from 0.95% after 81 days. However the initial release of Sample 1 was increased to 11% from 1.5% after 52 days.

TABLE 4

Summary of the stability of different microcapsules.

| | Time (Days) | REA | Time (days) | REA | Time (Days) | REA |
|---|---|---|---|---|---|---|
| Sample 1 | 3 | 1.5% | 52 | 11% | | |
| Sample 2 | 4 | 1.2% | 53 | 4.8% | | |
| Sample 8 | 4 | 0.95% | 32 | 1.1% | 81 | 1.8% |
| Sample 16 | 12 | 2.6% | 54 | 6.7% | 66 | 6.4% |

EXAMPLE 11

This illustrates a study of the microcapsules of the present invention by scanning electron microscope.

Figure 11:
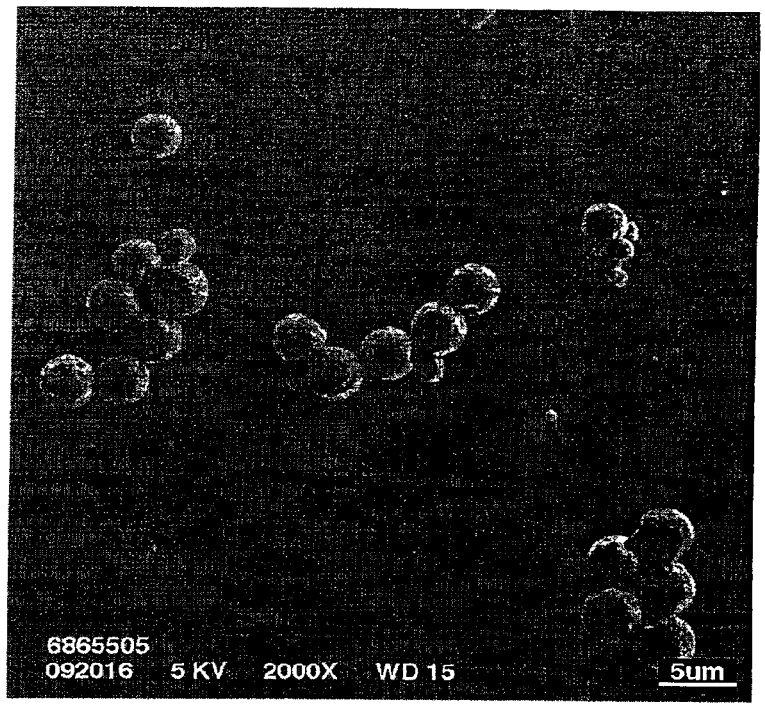
FIG. 11 is a scanning electron micrograph taken at 2000× of microcapsules of the present invention having a 50% by weight loading of silthiopham in the core and having a shell:core ratio of 30:100; a 5µ scale-bar illustrates the relative size of the microcapsules.

A sample of microcapsules containing silthiopham in the core was produced by the methods described in Example 6, except that the capsules had a 50% loading of silthiopham in the core with a shell wall:core ratio of 30:100, and mixing was carried out in a Waring blender as described in Example 7. The average particle size as measured by a Coulter counter was 2.4 microns, which is very close to what is observed by a scanning electron micrograph, which is shown in FIG. 11. The microcapsules have a spherical shape with some small dimples on the surface. Since the cores of these microcapsules contain 50% of silthiopham, the encapsulated active imposed some stress on the shell and thus the small dimple is believed to be associated with the stress appeared.

Figure 12:
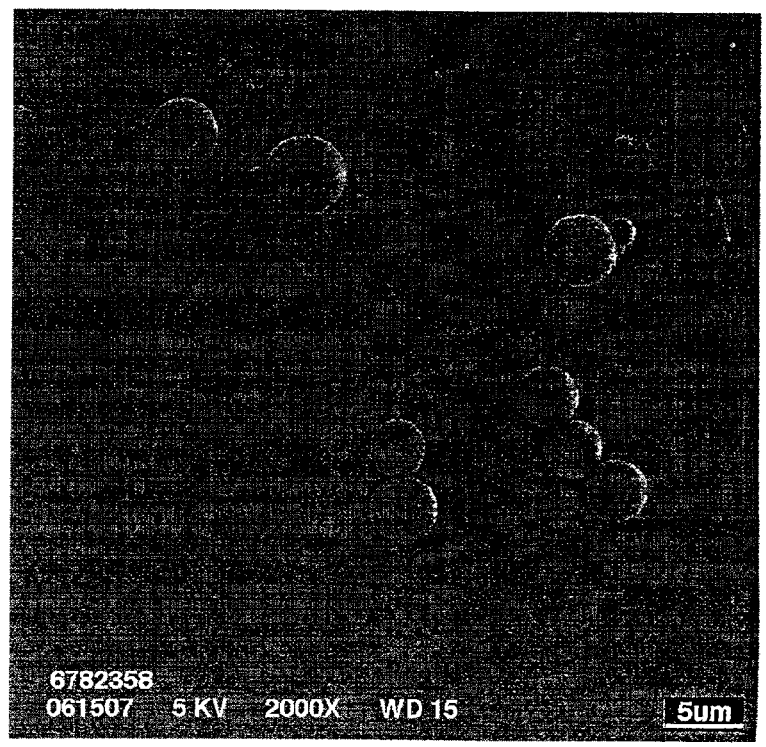
FIG. 12 is a scanning electron micrograph taken at 2000× of microcapsules of the present invention having a 32% by weight loading of silthiopham in the core and having a shell:core ratio of 30:100; a 5µ scale-bar illustrates the relative size of the microcapsules.

The sample shown in FIG. 12 has a 32% loading of silthiopham in the core with a shell wall:core ratio of 30:100. The average particle size as measured by a Coulter counter for this sample was 4.2 microns, which agrees with the size indicated by the SEM 5 μm bar. The microcapsules have a spherical shape and smooth surface. However the small dimples that were observed on the capsules of FIG. 11 were not observed on the surface of these capsules, and only one large dimple was observed on one of the microcapsules. Since this sample has a only 32% of silthiopham in the core, the stress from silthiopham on the shell is believed to be much smaller than for the capsules having higher levels of silthiopham.

EXAMPLE 12

This example illustrates the formation of a eutectic mixture with silthiopham and tebuconazole.

Figure 13:
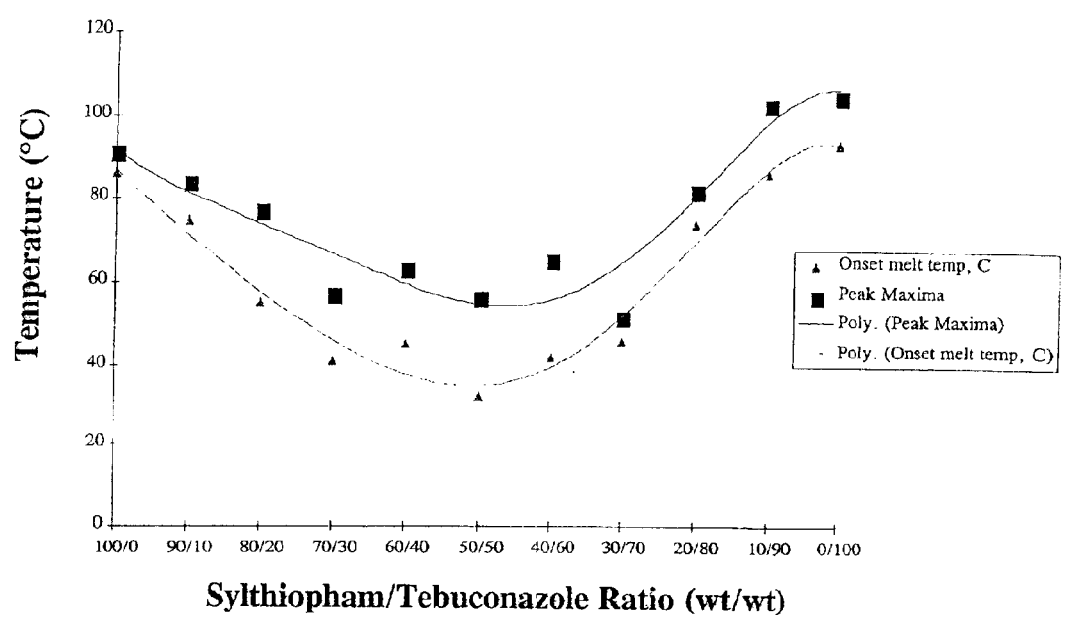
FIG. 13 is a plot of the melting point of a blend of silthiopham and tebuconazole as a function of the relative amounts of each of the components in the blend, and shows that the mixture forms a eutectic having a melting point approximately 26° C. lower than that of silthiopham at a ratio of about 50:50 by weight.

The melting temperature at one atmosphere was measured for pure silthiopham and for pure tebuconazole and for mixtures of 10:90, 20:80, 30:70, 40:60, 50:50, 60:40, 70:30, 80:20, and 90:10 silthiopham:tebuconazole, on a weight basis. The results are shown in FIG. 13, and indicate that the silthiopham/tebuconazole mixture forms a eutectic at about a 50:50 blend. The eutectic melting point appeared to be somewhat under 50° C., whereas the melting point of pure silthiopham is about 86° C. and the meting point of pure tebuconazole is somewhat over 100° C. This indicates that the eutectic mixture had a melting point that was over 35° C. lower than that of the lowest melting pure component (silthiopham, in this case).

EXAMPLE 13

This example illustrates the formation of a eutectic mixture with silthiopham and simeconazole.

Figure 14:
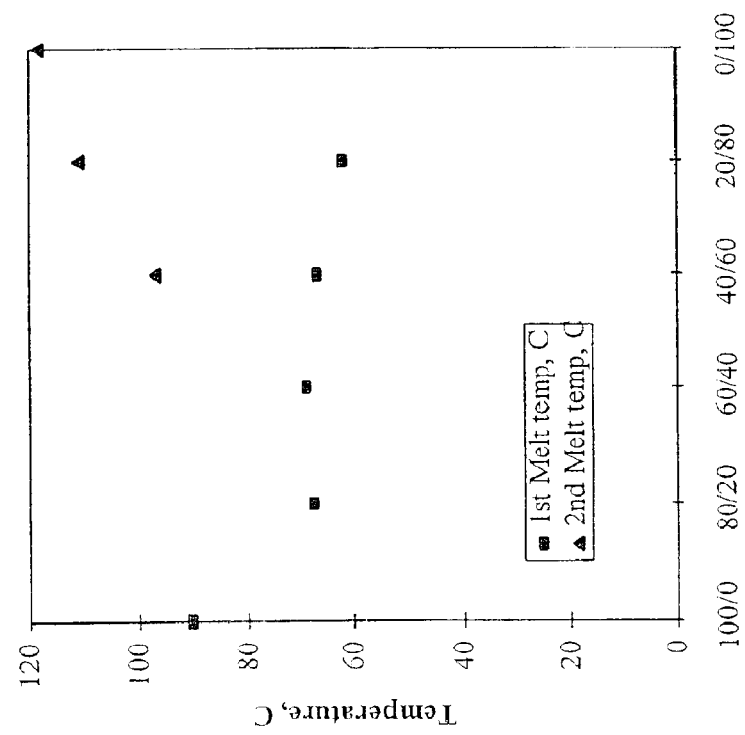
FIG. 14 is a plot of the melting point of a blend of silthiopham and simeconazole as a function of the relative amounts of each of the components in the blend, and shows that the mixture forms a eutectic having a melting point approximately 18° C. lower than that of silthiopham at a ratio of about 80:20 silthiopham:simeconazole by weight.

The melting temperature at one atmosphere was measured for pure silthiopham and for pure simeconazole and for mixtures of the two materials as described in Example 12. The results are shown in FIG. 14, and indicate that the silthiopham/simeconazole mixture forms a eutectic at a blend somewhere between 100:0 and 60:40, by weight. However, when the blend ratio was dropped to below about 50:50, by weight, two melting points were observed. The eutectic melting point appeared to be somewhat under 70° C., whereas the melting point of pure silthiopham is about 86° C. and the meting point of pure simeconazole is about 118° C. This indicates that the eutectic mixture had a melting point that was about 16° C. lower than that of the lowest melting pure component (silthiopham, in this case).

EXAMPLE 14

This example illustrates the formation of a eutectic mixture with silthiopham and 1-(4-fluorophenyl)-2-(1H-1,2,4-triazole-1-yl)-ethanone.

Figure 15:
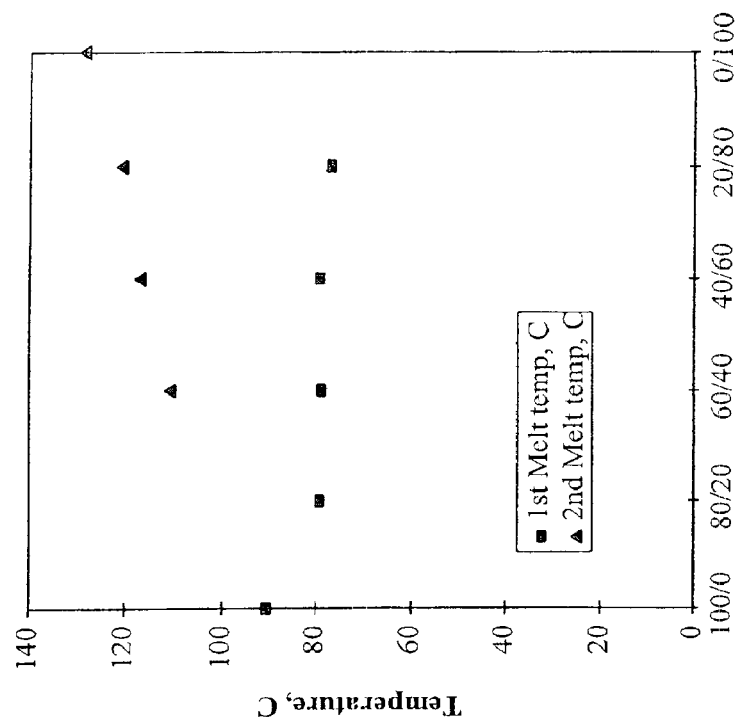
FIG. 15 is a plot of the melting point of a blend of silthiopham and fluorophenyltriazoleethanone as a function of the relative amounts of each of the components in the blend, and shows that the mixture forms a eutectic having a melting point approximately 6° C. lower than that of silthiopham at a ratio of about 80:20 silthiopham:fluorophenyltriazoleethanone by weight.

The melting temperature at one atmosphere was measured for pure silthiopham and for pure 1-(4-fluorophenyl)-2-(1H-1,2,4-triazole-1-yl)-ethanone and for mixtures of 10:90, 20:80, 30:70, 40:60, 50:50, 60:40, 70:30, 80:20, and 90:10 silthiopham: 1-(4-fluorophenyl)-2-(1H-1,2,4-triazole-1-yl)-ethanone, on a weight basis. The results are shown in FIG. 15, and indicate that the silthiopham/1-(4-fluorophenyl)-2-(1H-1,2,4-triazole-1-yl)-ethanone mixture forms a eutectic at a mixture somewhere between 100:0 and 60:40, by weight. The eutectic melting point appeared to be somewhat under 80° C., whereas the melting point of pure silthiopham is about 86° C. and the meting point of pure 1-(4-fluorophenyl)-2-(1H-1,2,4-triazole-1-yl)-ethanone is about 128° C. This indicates that the eutectic mixture had a melting point that was about 6° C. lower than that of the lowest melting pure component (silthiopham, in this case).

EXAMPLE 15

This example illustrates the production of microcapsules containing silthiopham and tebuconazole in the core and where the method is free of the use of a solvent.

An aqueous solution was prepared by adding Lomar D (5.16 g) to 90.4 g water in a 250 ml beaker, and the pH of the solution was adjusted to 7.2 by adding a small amount of citric acid. The solution was heated to 65° C. An organic liquid solution was prepared by intermixing silthiopham (25.00 g), tebuconazole (25.00 g), Desmodur N 3,200 (4.82 g) and TMXDI (1.58 g) and then heating the mixture until the solids were dissolved and the temperature of the solution was maintained at 65°–70° C. The aqueous solution was agitated with a Silverson S4RT-4 mixer equipped with a six hole screen for 5–10 seconds at 4,200 rpm and the organic solution was added into the agitated solution in 20 seconds. The mixture was further agitated at 9,500 to 10,200 rpm for 40 seconds. After the formed emulsion was transferred into a 400 ml beaker equipped with a mechanic stirrer set at 625 rpm, an amine solution containing water (4.00 g), triethylenetetramine (0.73 g) and Jeffamine T-403 (2.88 g) was added into the emulsion immediately. After maintaining the temperature of the mixture at 65°–70° C. for 0.5 hour, the isocyanate infrared absorbance peak at 2270 cm$^{-1}$ disappeared. 108.3 g of yellow slurry was collected after 1 hour. The weight ratio between the wall and the core was 20:100.

EXAMPLE 16

This illustrates the production of microcapsules containing silthiopham and tebuconazole in the absence of a solvent, but with a higher wall:core ratio that in Example 15.

Microcapsules were produced by the method described in Example 15, except that the organic solution contained 7.23 g of Desmodur N 3,200 and 2.37 g of TMXDI, and the amine solution contained 6.0 g of water, 1.1 g of triethylenetetramine and 4.32 g of Jeffamine T-403. The isocyanate peak at 2270 cm$^{-1}$ disappeared after 1.5 hours, and 107 g of a light yellow product was collected after 2 hours. The weight ratio between the wall and the core was 30:100.

EXAMPLE 17

This illustrates the production of microcapsules containing silthiopham and tebuconazole in the absence of a solvent, but with a higher wall:core ratio that in Example 15 and with only one type of amine.

Microcapsules were produced by the method described in Example 15, except that the organic solution contained 9.22 g of Desmodur N 3,200 and 3.03 g of TMXDI, and the amine solution contained 6.0 g of water, 2.8 g of triethylenetetramine (TETA) and no Jeffamine T-403. The isocyanate peak at 2270 cm$^{-1}$ disappeared after 2 hours, and 133 g of a light yellow product was collected after 2.25 hours. The weight ratio between the wall and the core was 30:100.

The product appears as a light yellow slurry and no crystals can be observed in the product under optical microscopy. The images from scanning electron microscopy (SEM) suggest that spherical microcapsules were formed.

EXAMPLE 18

This example illustrates the use of microcapsules formed according to the present invention to form a coating on wheat seed.

Wheat seed (100 g, of the species *triticum aestivum*, var. "Consort") was placed into the bowl of a Hege 11 seed coating machine. A sample (0.2 ml) of a formulation prepared according to the procedure of Example 1, but having a polyurea shell wall thickness of 30%, a concentration of silthiopham in the core of 60%, by weight, and an amine ratio between TETA and Jeffamine T403 of 50:50. This sample was diluted with water (0.8 ml) to afford a formulation with a silthiopham concentration of 125 g/1000 ml. This formulation was applied via syringe into the turning Hege bowl filled with wheat (100 g). The Hege bowl was turned on for 30 sec to provide uniform distribution and coating of seeds.

EXAMPLE 19

This example illustrates the use of microcapsules formed according to the present invention to form a coating on wheat seed.

The same procedure as described in Example 18 was used to coat wheat seed, except that 0.012 ml of Vinamul 18132 was added to the formulation containing the silthiopham. Wheat seed coated with the microcapsules of the present invention were obtained.

All references cited in this specification, including without limitation all papers, publications, patents, patent applications, presentations, texts, reports, manuscripts, brochures, books, internet postings, journal articles, periodicals, and the like, are hereby incorporated by reference. The discussion of the references herein is intended merely to summarize the assertions made by their authors and no admission is made that any reference constitutes prior art. Applicants reserve the right to challenge the accuracy and pertinency of the cited references.

In view of the above, it will be seen that the several advantages of the invention are achieved and other advantageous results obtained.

As various changes could be made in the above methods and compositions without departing from the scope of the invention, it is intended that all matter contained in the above description and shown in the accompanying drawings shall be interpreted as illustrative and not in a limiting sense.

What is claimed is:

1. A method of producing a controlled release form of a first agricultural active wherein the first agricultural active has low water solubility and a normal melting point above about 80° C., the method comprising providing an organic liquid composition which is free of solvents comprising forming a mixture comprising the first agricultural active and a melting point depressant; wherein the first agricultural active comprises a compound having the formula

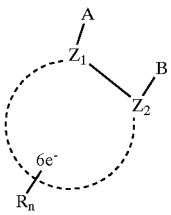

wherein $Z_1$ and $Z_2$ are C or N and are part of an aromatic ring selected from benzene, pyridine, thiophene, furan, pyrrole, pyrazole, thiazole, and isothiazole;

A is selected from —C(X)-amine, —C(O)—SR$_3$, —NH—C(X)R$_4$, and —C(=NR$_3$)—XR$_7$;

B is —W$_m$-Q(R$_2$)$_3$ or selected from o-tolyl, 1-naphthyl, 2-naphthyl, and 9-phenanthryl, each optionally substituted with halogen or R$_4$;

Q is C, Si, Ge, or Sn;

W is —$C(R_3)_pH_{(2-p)}$—; or when Q is C, W is selected from —$C(R_3)_pH_{(2-p)}$—, —$N(R_3)_mH_{(1-m)}$—, —S(O)$_p$—, and —O—;

X is O or S;

n is 0, 1, 2, or 3;

m is 0 or 1;

p is 0, 1, or 2;

each R is independently selected from a) halo, formyl, cyano, amino, nitro, thiocyanato, isothiocyanato, trimethylsilyl, and hydroxy;

b) $C_1$–$C_4$ alkyl, alkenyl, alkynyl, $C_3$–$C_6$ cycloalkyl, and cycloalkenyl, each optionally substituted with halo, hydroxy, thio, amino, nitro, cyano, formyl, phenyl, $C_1$–$C_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;

c) phenyl, furyl, thienyl, pyrrolyl, each optionally substituted with halo, formyl, cyano, amino, nitro, $C_1$–$C_4$ alkyl, alkenyl, alkynyl, alkoxy, alkylthio, alkylamino, dialkylamino, haloalkyl, and haloalkenyl;

d) $C_1$–$C_4$ alkoxy, alkenoxy, alkynoxy, $C_3$–$C_6$ cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo;

wherein two R groups may be combined to form a fused ring;

each $R_2$ is independently selected from alkyl, alkenyl, alkynyl, cycloalkyl, cycloalkenyl and phenyl, each optionally substituted with $R_4$ or halogen; and wherein, when Q is C, $R_2$ may also be selected from halo, alkoxy, alkylthio, alkylamino, and dialkylamino;

wherein two $R_2$ groups may be combined to form a cyclo group with Q;

$R_3$ is $C_1$–$C_4$ alkyl;

$R_4$ is $C_1$–$C_4$ alkyl, haloalkyl, alkoxy, alkylthio, alkylamino, or dialkylamino;

$R_7$ is $C_1$–$C_4$ alkyl, haloalkyl, or phenyl, optionally substituted with halo, nitro, or $R_4$;

or an agronomic salt thereof;

and wherein the melting point depressant comprises a fungicide selected from the group consisting of tebuconazole, simeconazole, tetraconazole, difenoconazole, fluquinconazole, fludioxonil, captan, metalaxyl, carboxin, and thiram;

forming the liquid composition into small droplets while maintaining said liquid composition at a temperature below the normal melting point of the first agricultural active; and enclosing each droplet in a non-water soluble shell to form a microcapsule.

2. The method according to claim 1, wherein the first agricultural active comprises a material having the formula 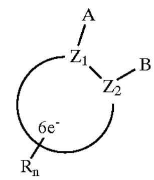 wherein $Z_1$ and $Z_2$ are C or N and are part of an aromatic ring which is thiophene;

A is selected from —C(X)-amine, wherein the amine is substituted with a first and a second amine substituent or with an alkylaminocarbonyl and a hydrogen, —C(O)—$SR_3$, —NH—C(X)$R_4$, and —C(=$NR_3$)—$XR_7$;

the first amine substituent which is selected from the group consisting of $C_1$–$C_{10}$ straight or branched alkyl, alkenyl, or alkylaryl groups or mixtures thereof optionally substituted with one or more halogen, hydroxy, alkoxy, alkylthio, nitrile, alkylsulfonate, haloalkylsulfonate, phenyl, $C_3$–$C_6$ cyclocalkyl and $C_5$–$C_6$ cycloalkynel; phenyl optionally substituted with one or more $C_1$–$C_4$ straight or branched alkyl, alkenyl, or alkynyl groups or mixtures thereof, cycloalkyl, cycloalkenyl, haloalkyl, alkoxy and nitro; $C_3$–$C_6$ cycloalkyl, $C_5$–$C_6$ cycloalkenyl, alkoxy, alkenoxy, alkynoxy, dialkylamino, and alkylthio;

and the second amine substituent which is selected from the group consisting of hydrogen; $C_1$–$C_6$ straight or branched alkyl, alkenyl, or alkynyl groups or mixtures thereof optionally substituted with one or more halogen; hydroxy, alkylcarbonyl, haloalkylcarbonyl, alkoxycarbonyl, and dialkylcarbonyl;

B is —$W_m$-Q$(R_2)_3$ or selected from o-tolyl, 1-naphthyl, 2-naphthyl, and 9-phenanthryl, each optionally substituted with halogen or $R_4$;

Q is C, Si, Ge, or Sn;

W is —$C(R_3)_pH_{(2-p)}$—; or when Q is C, W is selected from —$C(R_3)_pH_{(2-p)}$—, —$N(R_3)_mH_{(1-m)}$—, —S(O)$_p$—, and —C—;

X is O or S;

n is 2;

m is 0 or 1;

p is 0, 1, or 2;

wherein two R groups are combined to form a nonheterocyclic ring fused with the thiophene ring, which is not a benzothiophene other than a tetrahydrobenzothiophene, said two R groups being selected from the group consisting of $C_1$–$C_4$ alkyl, alkenyl, $C_3$–$C_6$ cycloalkyl and cycloalkenyl, each optionally substituted with hydroxy, thio, phenyl, $C_1$–$C_4$ alkoxy, alkylthio, alkylsulfinyl, or alkylsulfonyl;

each $R_2$ is independently selected from alkyl, alkenyl, alkynyl, cycloalkyl, cycloalkenyl and phenyl, each optionally substituted with $R_4$ or halogen; and wherein, when Q is C, $R_2$ may also be selected from halo, alkoxy, alkylthio, alkylamino, and dialkylamino; and further when Q is C, then two $R_2$ groups may be combined to form a cycloalkyl group with Q;

$R_3$ is $C_1$–$C_4$ alkyl;

$R_4$ is $C_1$–$C_4$ alkyl, haloalkyl, alkoxy, alkylthio, alkylamino, or dialkylamino; and $R_7$ is $C_1$–$C_4$ alkyl, haloalkyl, or phenyl optionally substituted with halo, nitro, or $R_4$;

or an agronomic salt thereof.

3. The method according to claim 1, wherein the mixture comprises a eutectic mixture.

4. The method according to claim 1, wherein the melting point depressant comprises tebuconazole.

5. The method according to claim 1, wherein the first agricultural active comprises silthiopham and the melting point of the mixture is a temperature that is at least about 5° C. lower than the melting point of silthiopham.

6. The method according to claim 5, wherein the melting point of the mixture is a temperature that is at least about 10° C. lower than the melting point of silthiopham.

7. The method according to claim 6, wherein the melting point of the mixture is a temperature that is at least about 15° C. lower than the melting point of silthiopham.

8. The method according to claim 7, wherein the melting point of the mixture is a temperature that is at least about 20° C. lower than the melting point of silthiopham.

9. The method according to claim 1, wherein the first agricultural active comprises silthiopham.

10. Microencapsulated silthiopham produced by the method of claim 9.

11. The method according to claim 9, wherein the mixture comprises silthiopham in an amount of at least about 5% by weight.

12. The method according to claim 11, wherein the mixture comprises silthiopham in an amount of at least about 25% by weight.

13. The method according to claim 12, wherein the mixture comprises silthiopham in an amount of at least about 50% by weight.

14. The method according to claim 9, wherein the mixture comprises in addition a second agricultural active.

15. The method according to claim 14, wherein the second agricultural active comprises a pesticide or a herbicide.

16. The method according to claim 15, wherein the second agricultural active comprises an insecticide, acaricide, bactericide, fungicide, nematocide, or molluscicide.

17. The method according to claim 16, wherein the second agricultural active comprises a fungicide selected from the group consisting of tebuconazole, simeconazole, fludioxonil, fluquinconazole, difenoconazole, 4,5-dimethyl-N-(2-propenyl)-2-(trimethylsilyl)-3-thiophenecarboxamide (sylthiopham), hexaconazole, etaconazole, propiconazole, triticonazole, flutriafol, epoxiconazole, fenbuconazole, bromuconazote, penconazole, imazalil, tetraconazole, flusilazole, metconazole, diniconazole, myclobutanil, triadimenol, bitertanol, pyremethanil, cyprodinil, tridemorph, fenpropimorph, kresoxim-methyl, azoxystrobin, ZEN90160, fenpiclonil, benalaxyl, furalaxyl, metalaxyl, R-metalaxyl, orfurace, oxadixyl, carboxin, prochloraz, trifulmizole, pyrifenox, acibenzolar-S-methyl, chlorothalonil, cymoaxnil, dimethomorph, famoxadone, quinoxyfen, fenpropidine, spiroxamine, triazoxide, BAS50001F, hymexazole, pencycuron, fenamidone, guazatine, and cyproconazole.

18. The method according to claim 16, wherein the second agricultural active comprises a fungicide selected from the group consisting of tebuconazole, tetraconazole, simeconazole, difenoconazole, fluquinconazole, fludioxonil, captan, metalaxyl, carboxin, and thiram.

19. The method according to claim 1, wherein the step of enclosing each droplet in a non-water soluble shell to provide a microcapsule comprises dispersing the small droplets of the organic liquid composition in an aqueous liquid which is immiscible with the organic liquid composition; and forming a non-water soluble shell by interfacial polymerization at the interface of the droplets and the aqueous liquid which shell encloses each droplet as a core of a microcapsule.

20. The method according to claim 19, wherein the organic liquid composition comprises one or more polyisocyanates;

the aqueous liquid comprises one or more polyamines; and wherein the interfacial polymerization comprises reaction of the polyisocyanates and the polyamines at the interface of the droplets and the aqueous liquid.

21. The method according to claim 20, wherein the one or more polyisocyanates comprise 1,12-dodecane diisocyanate, cyclobutane-1,3-diisocyanate, cyclohexane-1, 3-diisocyanate, 2,4- and/or 2,6-hexahydrotoluylene diisocyanate, 4,4',4"-triphenylmethane triisocyanate, tris-(4-isocyanatophenyl)-thiophosphate, 1,6-diisocyanate homopolymer, OCN—R—(O—CH$_2$CH$_2$)$_x$—R—NCO (polyethylene glycol), OCN—R—(OCH$_2$—CH—CH$_3$)$_x$—R—NCO (polypropylene glycol), OCN—R—(OCH$_2$CH$_2$CH$_2$CH$_2$)$_x$—R—NCO (polytetramethylene glycol), OCN—R—(OCH$_2$CH$_2$OCO—CH$_2$CH$_2$CH$_2$CH$_2$—CO)$_x$—R—NCO (polyethyleneadipate), OCN—R—(OCH$_2$CH$_2$CH$_2$CH$_2$OCO—CH$_2$CH$_2$CH$_2$CH$_2$—CO)$_x$—R—NCO (polybutyleneadipate), OCN—R—(OCH$_2$CH$_2$CH$_2$CH$_2$CH$_2$CH$_2$OCO)$_x$—R—NCO (polyhexamethylene-polycarbonate), where in each case, R can be CH$_2$ or CH$_2$CH$_2$ or alkyl, HDI, 1,5 Diisocyanatopentane, TMDI, C$_{12}$DI, 1,6,11-Undecanetriioscyanate, CHDI, BDI, HXDI, IPDI, IMCI, DDI-1410, XDI, m-TMXDI, p-TMXDI, DEBI, HMDI, OCN(CH$_2$)$_3$O(CH$_2$)$_3$NCO, OCN(CH$_2$)$_3$OCH$_2$CH$_2$O(CH$_2$)$_3$NCO, OCN(CH$_2$)3OCH(CH3)CH2O(CH2)3NCO, OCN(CH$_2$)$_3$O(CH$_2$)$_3$O(CH$_2$)$_3$NCO, OCN(CH$_2$)$_3$O(CH$_2$)$_2$O(CH$_2$)$_2$O(CH$_2$)$_3$NCO, OCN(CH$_2$)$_3$OCH(CH$_3$)CH(CH$_3$)O(CH$_2$)$_3$NCO, OCN(CH$_2$)$_3$OCH$_2$C(CH$_3$)$_2$CH$_2$O(CH$_2$)$_3$NCO, OCN(CH$_2$)$_3$OCH$_2$C(Et)$_2$CH$_2$O(CH$_2$)$_3$NCO,

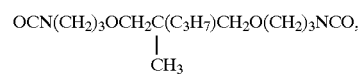

OCN(CH$_2$)$_3$O(CH$_2$)$_4$O(CH$_2$)$_3$NCO, OCN(CH$_2$)$_3$O(CH$_2$)$_6$O(CH$_2$)$_3$NCO, OCN(CH$_2$)$_3$O(CH$_2$)$_{10}$O(CH$_2$)$_3$NCO, PPDI, 2,4-TDI, TDI(80:20), MDI, PMDI, NDI, TODI, and mixtures thereof.

22. The method according to claim 20, wherein the one or more polyisocyanates are selected from the group consisting of N,N',N"-tris(6-isocyanatohexyl)-nitrodotricarbonic triamide and meta-tetramethylenexylylene diisocyanate.

23. The method according to claim 22, wherein the one or more polyisocyanates comprise N,N',N"-tris(6-isocyanatohexyl)-nitrodotricarbonic triamide and meta-tetramethylenexylylene diisocyanate.

24. The method according to claim 20, wherein the one or more polyamines comprise a polyamine selected from the group consisting of diethylene triamine, triethylene tetramine, tetraethylene pentamine, iminobispropylamines, amine epoxy adducts, alkyldiamines from ethylene diamine to hexamethylene diamine, and trimethylolpropane tris[poly(propylene glycol)amine terminated]ether.

25. The method according to claim 24, wherein the one or more polyamines comprise at least two polyamines selected from the groups consisting of diamines, triamines and tetramines.

26. The method according to claim 25, wherein the one or more polyamines comprise at least one triamine and at least one tetramine.

27. The method according to claim 21, wherein the one or more polyamines are selected from the group consisting of diethylene triamine, tetraethylene pentamine, triethylene tetramine, iminobispropylamines, amine epoxy adducts, alkyldiamines from ethylene diamine to hexamethylene diamine, and trimethyloipropane tris(poly(propylene glycol) amine terminated)ether.

28. The method according to claim 27, wherein the one or more polyamines are selected from the group consisting of triethylenetetramine and trimethyloipropane tris[poly(propylene glycol)amine terminated]ether.

29. The method according to claim 28, wherein the one or more polyamines comprise triethylenetetramine and trimethylolpropane tris(poly(propylene glycol)amine terminated)ether.

30. The method according to claim 19, wherein the aqueous liquid comprises water.

31. The method according to claim 19, wherein the reaction of the one or more polyisocyanates with the one or more polyamines is carried out at a temperature of between about 25° C. and about 90° C.

32. The method according to claim 31, wherein the reaction of the one or more polyisocyanates and the one or more polyamines is carried out at a temperature of between about 40° C. and about 75° C.

33. The method according to claim 19, wherein the ratio of the equivalents of polyisocyanates to the equivalents of polyamines is between about 4:1 to about 1:4.

34. The method according to claim 33, wherein the ratio of the equivalents of polyisocyanates to the equivalents of polyamines is between about 2:1 to about 1:2.

35. The method according to claim 34, wherein the ratio of the equivalents of polyisocyanates to the equivalents of polyamines is about 1:1.

36. The method according to claim 33, wherein the one or more polyamines comprise at least one triamine and at least one tetramine present in an equivalents ratio of triamine:tetramine of from about 100:0 to about 0:100.

37. The method according to claim 36, wherein the one or more polyamines comprise at least one triamine and at least one tetramine present in an equivalents ratio of triamine:tetramine of from about 20:80 to about 80:20.

38. The method according to claim 37, wherein the one or more polyamines comprise at least one triamine and at least one tetramine present in an equivalents ratio of triamine:tetramine of from about 40:60 to about 60:40.

39. The method according to claim 38, wherein the one or more polyamines comprise at least one triamine and at least one tetramine present in an equivalents ratio of triamine:tetramine of from about 50:50.

40. The method according to claim 19, wherein an emulsifier is also present.

41. The method according to claim 40, wherein the emulsifier is selected from a material comprising a sodium salt of naphthalene sulfonic acid formaldehyde polymer and a sodium salt of maleic acid copolymer.

42. The method according to claim 19, wherein the pH of the solution is adjusted to between about 4 and about 11 by the addition of citric acid.

43. The method according to claim 42, wherein the pH of the solution is adjusted to between about 5 and about 9 by the addition of citric acid.

44. The method according to claim 43, wherein the pH of the solution is adjusted to between about 7 and about 8 by the addition of citric acid.

45. The method according to claim 19, wherein the weight ratio of the shell to the core is from about 5:100 to about 50:100.

46. The method according to claim 45, wherein the weight ratio of the shell to the core is from about 10:100 to about 40:100.

47. The method according to claim 46, wherein the weight ratio of the shell to the core is from about 15:100 to about 30:100.

48. The method according to claim 19, wherein the microcapsules have an average particle size of from $1\mu$ to $20\mu$.

49. The method according to claim 48, wherein the microcapsules have an average particle size of from $2\mu$ to $10\mu$.

50. The method according to claim 49, wherein the microcapsules have an average particle size of from $2\mu$ to $8\mu$.

51. The method according to claim 50, wherein the microcapsules have an average particle size of from $2\mu$ to $6\mu$.

\* \* \* \* \*

UNITED STATES PATENT AND TRADEMARK OFFICE
CERTIFICATE OF CORRECTION

PATENT NO. : 6,992,047 B2
DATED : January 31, 2006
INVENTOR(S) : Jawed Asrar and Yiwei Ding It is certified that error appears in the above-identified patent and that said Letters Patent is hereby corrected as shown below:

<u>Column 41, line 62 through Column 44, line 42,</u>
Delete claims 19 through 51.

Signed and Sealed this

Eighteenth Day of April, 2006

JON W. DUDAS
*Director of the United States Patent and Trademark Office*

UNITED STATES PATENT AND TRADEMARK OFFICE
CERTIFICATE OF CORRECTION

PATENT NO. : 6,992,047 B2  Page 1 of 1
APPLICATION NO. : 10/115765
DATED : January 31, 2006
INVENTOR(S) : Jawed Asrar and Yiwei Ding It is certified that error appears in the above-identified patent and that said Letters Patent is hereby corrected as shown below:

Column 5,
Line 36, insert -- O -- between "X is" and "or S;".
Line 37, insert -- 0 -- between "n is" and "1, 2, or 3;".

Column 24,
Line 39, replace "%" with -- µ --.

Column 25,
Lines 18 and 19, delete "(1,6-diisocyanate homo-polymer, available from Bayer Corporation, Pittsburgh, Pa.),".

Column 31,
Line 45, replace "Notetime." with -- Note time. --.

Column 33,
Line 59, replace "4.1%" with -- 4.1 µ --.

Column 40,
Line 41, replace "-C-" with -- -O- --.

Signed and Sealed this

Twenty-seventh Day of June, 2006

JON W. DUDAS
*Director of the United States Patent and Trademark Office*